US009119365B2

(12) United States Patent
Kerns et al.

(10) Patent No.: US 9,119,365 B2
(45) Date of Patent: Sep. 1, 2015

(54) METHODS AND COMPOSITIONS FOR GOSS' WILT RESISTANCE IN CORN

(71) Applicant: Monsanto Technology LLC, St. Louis, MO (US)

(72) Inventors: Michael R. Kerns, Ankeny, IA (US); Hongwu Jia, Mystic, CT (US); David Butruille, Urbandale, IA (US); Travis J. Frey, Brentwood, MO (US); Kevin Cook, Ankeny, IA (US); Laron Peters, Gothenburg, NE (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/294,351

(22) Filed: Jun. 3, 2014

(65) Prior Publication Data
US 2014/0283222 A1 Sep. 18, 2014

Related U.S. Application Data

(63) Continuation of application No. 13/742,042, filed on Jan. 15, 2013, now Pat. No. 8,766,035, which is a continuation of application No. 12/201,206, filed on Aug. 29, 2008, now abandoned.

(60) Provisional application No. 60/966,706, filed on Aug. 29, 2007.

(51) Int. Cl.
*C12Q 1/68* (2006.01)
*A01H 5/10* (2006.01)
*A01H 1/04* (2006.01)

(52) U.S. Cl.
CPC .. *A01H 5/10* (2013.01); *A01H 1/04* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 5,574,210 A | 11/1996 | Saghai-Maroof et al. | |
| 5,749,169 A | 5/1998 | Briggs | |
| 5,773,682 A | 6/1998 | Roundy | |
| 6,399,855 B1 | 6/2002 | Beavis | |
| 7,247,776 B1 | 7/2007 | Stelpflug | |
| 7,973,212 B2 | 7/2011 | Sebastian | |
| 2004/0025202 A1 | 2/2004 | Laurie et al. | |
| 2007/0015164 A1 | 1/2007 | Khatib | |
| 2007/0039065 A1 | 2/2007 | Laurie | |
| 2008/0083042 A1 | 4/2008 | Butruille et al. | |
| 2009/0064360 A1 | 3/2009 | Kerns et al. | |
| 2009/0064361 A1 | 3/2009 | Butruille et al. | |
| 2009/0070903 A1 | 3/2009 | Kerns et al. | |
| 2009/0172845 A1 | 7/2009 | Li et al. | |
| 2010/0146657 A1 | 6/2010 | Butruille et al. | |
| 2012/0324599 A1 | 12/2012 | Kerns et al. | |

FOREIGN PATENT DOCUMENTS

| | | |
|---|---|---|
| CN | 1443440 A | 9/2003 |
| WO | 01/49104 A2 | 7/2001 |
| WO | 2007103786 A2 | 9/2007 |
| WO | 2008021225 A2 | 2/2008 |
| WO | 2008021413 A1 | 2/2008 |
| WO | 2008042185 A2 | 4/2008 |
| WO | 2009002924 A1 | 12/2008 |

OTHER PUBLICATIONS

Laurie et al., Accession No. ADJ48022 (2004).
Zhang et al., "Induction and Identification of Haploids of Advanced Hybridization of Transgenic Bt Upland Cotton", Shandong Agricultural Sciences, 2003, pp. 11-14, 34, Issue 4, China Academic Journal Electronic Publishing House.
Treat C.L. et al., "Inheritance of Resistance to Goss's Wilt in Sweet Corn", J. Amer. Soc. Hort. Sci., 1990, pp. 672-674, vol. 115, No. 4.
Whitelaw et al., Accession Nos. CG104426; effective filing date Aug. 22, 2003.
Whitelaw et al., Accession Nos. CG214340; effective filing date Aug. 22, 2003.
Accession No. AY104983 (2004).
Co-Pending U.S. Appl. No. 14/015,338 entitled "Methods and Compositions for Gray Leaf Spot Resistance in Corn" filed Aug. 30, 2013.
Arus et al., "Marker-Assisted Selection", Plant Breeding: Principles and Prospects, 1993, pp. 314-331, Chapman & Hall, London.
Bajaj et al., "In Vitro Production of Haploids and Their Use in Cell Genetics and Plant Breeding", Biotechnology in Agriculture and Forestry, Jan. 1, 1990, pp. 3-44, vol. 12.
Bink et al., "Fine Mapping of Quantitative Trait Loci Using Linkage Disequilibrium in Inbred Plant Populations", Euphytica, 2004, pp. 95-99, vol. 137.
Brown et al., "Quantitative Trait Loci in Sweet Corn Associated with Partial Resistance to Stewart's Wilt, Northern Corn Leaf Blight, and Common Rust", Phytopathology, Mar. 2001, pp. 293-300, vol. 91, No. 3.
Bubeck et al., "Quantitative Trait Loci Controlling Resistance to Gray Leaf Spot in Maize", Crop Science, Jan. 1, 1993, pp. 838-847, vol. 33, No. 4, Crop Science Society of America, Madison, WI, US.
Carson, M.L. et al, "Pathogenicity, Aggresiveness, and Virulence of Three Species of *Cercospora* Associated with Gray Leaf Spot of Maize", Maydica, 2006, pp. 89-92, vol. 51.

(Continued)

*Primary Examiner* — Medina A Ibrahim
(74) *Attorney, Agent, or Firm* — Thompson Coburn LLP; William A. Holtz

(57) ABSTRACT

The present invention relates to the field of plant breeding. More specifically, the present invention includes a method of using haploid plants for genetic mapping of traits of interest such as disease resistance. Further, the invention includes a method for breeding corn plants containing quantitative trait loci (QTL) that are associated with resistance to Goss' Wilt, a bacterial disease associated with *Clavibacter michiganense* spp.

15 Claims, 10 Drawing Sheets

(56) References Cited

OTHER PUBLICATIONS

Carson, M.L. et al, "Variation in Aggressiveness Among Isolates of *Cercospora* from Maize as a Potential Cause of Genotype-Environment Interaction in Gray Leaf Spot Trials", Plant Disease, Oct. 2002, pp. 1089-1093, vol. 86.
Chebotar et al., "The Use of Maternal Haploids for Genetic Analysis of the Number of Kernel Rows Per Ear in Maize", Hereditas, 1996, pp. 173-178, vol. 124, No. 2.
Chebotar et al., "Use of Matroclinous Haploids for Genetic Analysis of Ear Length and Plant Height in Maize", Genetika, 1996, 1 page (abstract only), vol. 32, No. 6.
Chen et al., "Genetic Analysis of Anther-Derived Plants of Rice", Journal of Heredity, 1982, pp. 49-52, vol. 73.
Clements, M.J. et al, "Quantitative Trait Loci Associated with Resistance to Gray Leaf Spot of Corn", Phytopathology, 2000, pp. 1018-1025, vol. 990, No. 9.
Dempster et al., "Maximum Likelihood from Incomplete Data via the EM Algorithm", Journal of the Royal Statistical Society, 1977, pp. 1-38, vol. 39, No. 1.
Excoffier et al., "Maximum-Likelihood Estimation of Molecular Haplotype Frequencies in a Diploid Population", Molecular Biology and Evolution, 1995, pp. 921-927, vol. 12, No. 5.
Fan et al., "High-Resolution Association Mapping of Quantitative Trait Loci: A Population-Based Approach", Genetics, Jan. 2006, pp. 663-686, vol. 172.
Gasbarra et al., "Constructing the Parental Linkage Phase and the Genetic Map Over Distances <1 cM Using Pooled Haploid DNA", Genetics, 2006, pp. 1325-1335, vol. 172.
Gordon, Stuart G. et al, "Linkage of Molecular Markers to *Cercospora zeae-maydis* Resistance in Maize", Crop Science, 2004, pp. 628-636, vol. 44.
Greenland et al., "Reversible male sterility: a novel system for the porduction of hybrid corn", Symp Soc Exp Biol, 1998, pp. 141-147, vol. 51.
Hiebert et al., "Locating the Broad-Spectrum Wheat Leaf Rust Resistance Gene Lr52 (LrW) to Chromosome 5B by a New Cytogenetic Method", Theoretical and Applied Genetics; International Journal of Plant Breeding Research, May 1, 2005, pp. 1453-1457, vol. 110, No. 8.
Jansen et al., "Genotype-by-Environment Interaction in Genetic Mapping of Multiple Quantitative Trait Loci", Theoretical and Applied Genetics, 1995, pp. 33-37, vol. 91.
Jansen et al., "High Resolution of Quantitative Traits Into Multiple Loci via Interval Mapping", Genetics, Apr. 1994, pp. 1447-1455, vol. 136.
Jansen, "Mapping of Quantitative Trait Loci by Using Genetic Markers: An Overview of Biometrical Models Used", Biometrics in Plant Breeding: Applications of Molecular Markers, Proceedings of the Ninth Meeting of the Eucarpia Section Biometrics in Plant Breeding, van Oijen, Jansen (eds.), 1994, pp. 116-124, The Netherlands.
Kruglyak et al., "A Nonparametric Approach for Mapping Quantitative Trait Loci", Genetics, Mar. 1995, pp. 1421-1428, vol. 139.
Lander et al., "Mapping Mendelian Factors Underlying Quantitative Traits Using RFLP Linkage Maps", Genetics, Jan. 1989, pp. 185-199, vol. 121.
Lehmensiek et al., "Genetic Mapping of Gray Leaf Spot (GLS) Resistance Genes in Maize", Theoretical and Applied Genetics, Oct. 1, 2001, pp. 797-803, vol. 103, No. 5.
Li et al., "Haplotype-Based Quantitative Trait Mapping Using a Clustering Algorithm", BMC Bioinformatics, May 18, 2006, pp. 1-11, vol. 7, No. 258.
Li et al., "Multivariate Survival Models Induced by Genetic Frailties, With Application to Linkage Analysis", Biostatistics, 2002, pp. 57-75, vol. 3.
Liu et al., "Mapping PrBn and Other Quantitative Trait Loci Responsible for the Control of Homeologous Chromosome Pairing in Oilseed Rape (*Brassica napus* L.) Haploids", Genetics, 2006, pp. 1583-1596, vol. 174, No. 3.
Ortiz et al., "Use of Haploids and Isozyme Markers for Genetic Analysis in the Polysomic Polyploid Potato", J. Genet. & Breed., 1993, pp. 283-288, vol. 47.
Paul, P.A., et al, "Regression and Artificial Neural Network Modeling for the Prediction of Gray Leaf Spot of Maize", Phytopathology, 2005, pp. 388-396, vol. 95.
Pret'ova et al., "Haploid Formation in Maize, Barley, Flax, and Potato", Protoplasma: An International Journal of Cell Biology, Aug. 31, 2006, pp. 107-114, vol. 228, No. 1-3.
Rober et al., "In Vivo Haploid Induction in Maize—Performance of New Inducers and Significance of Doubled Haploid Lines in Hybrid Breeding", Maydica, 2005, pp. 275-283, vol. 50.
Rocheford et al., "Genetic Studies of Resistance in Maize (*Zea mays* L.) to Goss's Bacterial Wilt and Blight (*Clavibacter michiganense* ssp. *nebraskense*)", Journal of Heredity, 1989, p. 351-356, vol. 80, No. 5.
Rotarenco, "Segregation for the Marker ra1 Gene in Matroclinal Haploids of Maize", Maize Genetics Cooperation Newsletter, 2000, pp. 1-2, vol. 74.
Saghai Maroof, M.A. et al., "Analysis of the Barley and Rice Genomes by Comparative RFLP Linkage Mapping", Theoretical and Applied Genetics, 1996, pp. 541-551, vol. 92.
Saghai Maroof, M.A., et al, "Identfcation of Quantitative Trait Loci Controlling Resistance to Gray Leaf Spot Disease in Maize", Theoretical and Applied Genetics, 1996, pp. 539-546, vol. 93.
Song et al., "A Comparison of Genetic Maps Constructed from Haploid and BC1 Mapping Populations From the Same Crossing Between *Gossypium hirsutum* L and *Gossypium barbadense*", Genome, 2005, pp. 378-390, vol. 48.
Tanksley et al., "Molecular Mapping of Plant Chromosomes", Chromosome Structure and Function: Impact of New Concepts, 1988, pp. 157-173, J.P. Gustafson and R. Appels (eds.), Plenum Press, New York.
Utz et al., "Comparison of Different Approaches to Interval Mapping of Quantitative Trait Loci", Biometrics in Plant Breeding: Applications of Molecular Markers, Proceedings of the Ninth Meeting of the Eucarpia Section Biometrics in Plant Breeding, van Oijen, Jansen (eds.), 1994, pp. 195-204, The Netherlands.
Varrieur, "AFLP Marker Analysis of Monoploid Potato", Thesis submitted to faculty of Virginia Polytechnic Institute and State University, 2002, pp. 1-90.
Ward Julian M, et al, "Gray Leaf Spot: A Disease of Global Importance in Maize Production", Plant Disease, 1999, pp. 884-895, vol. 83, No. 10.
Wych, Robert D., "Production of Hybrid Seed Corn", Corn and Corn Improvement (Third Edition), 1988, pp. 565-607, No. 18 in the series "Agronomy".
Yadav et al., "Mapping Genes Controlling Root Morphology and Root Distribution in a Doubled-Haploid Population of Rice", Theoretical and Applied Genetics, 1997, pp. 619-632, vol. 94.
Zeng, "Precision Mapping of Quantitative Trait Loci", Genetics, Apr. 1994, pp. 1457-1468, vol. 136.
Balint-Kurti et al., "Use of an Advanced Intercross Line Population for Precise Mapping of Quantitative Trait Loci for Gray Leaf Spot Resistance in Maize", Crop Science, 2008, pp. 1696-1704, vol. 48.
Coates et al., "Sources of Resistance to Gray Leaf Spot of Corn", Plant Disease, 1994, pp. 1153-1155, vol. 78 No. 12.
Coates et al., "Inheritance of Resistance to Gray Leaf Sport in Crosses Involving Selected Resistant Inbred Lines of Corn", Phytopathology, 1998, pp. 972-982, vol. 88 No. 9.
Juliatti et al., "Genetic mapping for resistance to gray leaf spot in maize", Euphytica, 2009, pp. 227-238, vol. 169.
Danson et al., "Quantitative trait loci (QTLs) for resistance to gray leaf spot and common rust diseases of maize", African Journal of Biotechnology, 2008, pp. 3247-3254, vol. 7 No. 18.
Derera et al., "Gene Action Controlling Gray Leaf Spot Resistance in Southern African Maize Germplasm", Crop Science, 2008, pp. 93-98, vol. 48.
Pozar et al., "Mapping and validation of quantitative trait loci for resistance to *Cercospora zeae-maydis* infection in tropical maize (*Zea mays* L)", Theoretical and Applied Genetics, 2009, pp. 553-564, vol. 118.

Figure 1. Markers associated with resistance to Goss' Wilt. "*" represents a single nucleotide deletion.

| QTL | Marker | Chr | pos | Sig | effect | res allele | Mapping Study | Fav. Parent | SNP Position | SEQ ID |
|---|---|---|---|---|---|---|---|---|---|---|
| 1 | NC0154927 | 1 | 18.5 | 0.04686 | 0.009544 | C | Study 1 | CV012 | 350 | 13 |
| 2 | NC0001369 | 1 | 24.3 | 0.010408 | 0.011109 | G | Study 1 | CV012 | 148 | 1234 |
| 2 | NC0110473 | 1 | 24.6 | 0.0006 | 0.108612 | T | Study 2 | | 194 | 19 |
| 3 | NC0003563 | 1 | 34.5 | 2.95E-05 | 0.269505 | G | Study 3 | | 434 | 27 |
| 4 | NC0052741 | 1 | 49.5 | 0.011696 | 0.085539 | G | Study 3 | | 411 | 36 |
| 5 | NC0113502 | 1 | 63.5 | 0.001533 | 0.221549 | G | Study 3 | | 447 | 50 |
| 5 | NC0039840 | 1 | 65.8 | <.0001 | 0.154467 | G | Study 2 | | 82 | 53 |
| 6 | NC0025863 | 1 | 96.7 | 0.013297 | -0.00703 | G | Study 1 | CV085 | 107 | 90 |
| 7 | NC0016873 | 1 | 101 | 0.024053 | 0.013666 | G | Study 4 | | 35 | 94 |
| 7 | NC0015205 | 1 | 101.5 | 0.00982 | -0.01944 | C | Study 1 | CV085 | 401 | 95 |
| 7 | NC0011522 | 1 | 103.1 | 0.001129 | 0.006155 | C | Study 4 | | 250 | 97 |
| 7 | NC0005280 | 1 | 103.2 | 0.000227 | -0.04657 | A | Study 4 | | 141 | 1235 |
| 7 | NC0053351 | 1 | 103.3 | 0.019659 | -0.00398 | C | Study 4 | | 235 | 1236 |
| 7 | NC0027375 | 1 | 103.7 | 0.005067 | 0.0095 | G | Study 4 | | 474 | 99 |
| 7 | NC0038741 | 1 | 103.7 | 0.016397 | 0.151215 | A | Study 3 | | 239 | 101 |
| 7 | NC0066981 | 1 | 103.7 | 0.002375 | -0.04438 | C | Study 4 | | 147 | 102 |
| 7 | NC0069188 | 1 | 103.7 | 0.00252 | -0.00778 | C | Study 4 | | 145 | 1237 |
| 7 | NC0008984 | 1 | 105.5 | 0.003146 | -0.05495 | — | Study 4 | | 376 | 106 |
| 7 | NC0039416 | 1 | 105.9 | 0.007911 | 0 | * | Study 4 | | 530 | 1238 |
| 7 | NC0041836 | 1 | 107.7 | 0.000879 | 0.035135 | C | Study 4 | | 92 | 110 |
| 7 | NC0014644 | 1 | 107.8 | 0.011101 | -0.01058 | — | Study 4 | | 485 | 111 |
| 7 | NC0037068 | 1 | 108.3 | 0.011592 | 0 | ********* | Study 4 | | 164 | 1239 |
| 7 | NC0037068 | 1 | 108.3 | 0.039253 | -0.00601 | G | Study 1 | CV085 | 164 | 1239 |
| 8 | NC0113263 | 1 | 110.1 | 0.005381 | 0.054854 | A | Study 4 | | 216 | 1240 |
| 8 | NC0033728 | 1 | 113.3 | 0.003777 | -0.0342 | C | Study 4 | | 83 | 119 |
| 8 | NC0002688 | 1 | 114.6 | <.0001 | -0.29232 | C | Study 2 | | 69 | 121 |
| 8 | NC0004176 | 1 | 116.3 | 0.00019 | 0.073238 | A | Study 4 | | 61 | 122 |
| 8 | NC0039351 | 1 | 118.8 | 0.000128 | -0.045 | G | Study 4 | | 678 | 124 |
| 8 | NC0039351 | 1 | 118.8 | 0.015782 | 0.077241 | GAGAG | Study 3 | | 678 | 124 |
| 9 | NC0035132 | 1 | 121.5 | 0.022545 | -0.11069 | ***** | Study 4 | | 394 | 128 |
| 9 | NC0035132 | 1 | 121.5 | 0.006728 | -0.00789 | C | Study 1 | CV085 | 394 | 128 |
| 9 | NC0034627 | 1 | 126 | 0.000266 | 0.232974 | C | Study 3 | | 415 | 130 |
| 9 | NC0035547 | 1 | 126 | 0.017288 | 0.040442 | T | Study 4 | | 190 | 131 |

FIGURE 1

| QTL | Marker | Chr | pos | Sig | effect | res allele | Mapping Study | Fav. Parent | SNP Position | SEQ ID |
|---|---|---|---|---|---|---|---|---|---|---|
| 9 | NC0039531 | 1 | 126 | 0.00037 | 0.114735 | G | Study 4 | -- | 215 | 132 |
| 10 | NC0107077 | 1 | 130.7 | 0.017758 | -0.01797 | A | Study 1 | CV085 | 380 | 136 |
| 10 | NC0107077 | 1 | 130.7 | 0.002565 | -0.0087 | A | Study 1 | CV085 | 380 | 136 |
| 10 | NC0008719 | 1 | 137.1 | 0.027094 | -0.0514 | A | Study 4 | -- | 244 | 138 |
| 10 | NC0008719 | 1 | 137.1 | 0.003405 | -0.02195 | A | Study 1 | CV085 | 244 | 138 |
| 10 | NC0008719 | 1 | 137.1 | 0.032113 | -0.00605 | A | Study 1 | CV085 | 244 | 138 |
| 11 | NC0024096 | 1 | 145.2 | 5.51E-05 | 0.254406 | T | Study 3 | -- | 212 | 141 |
| 11 | NC0024096 | 1 | 145.2 | 0.012609 | -0.01848 | G | Study 1 | CV085 | 212 | 141 |
| 11 | NC0024096 | 1 | 145.2 | 0.004333 | -0.01243 | G | Study 1 | CV010 | 212 | 141 |
| 11 | NC0024096 | 1 | 145.2 | 0.006585 | -0.00764 | G | Study 1 | CV085 | 212 | 141 |
| 12 | NC0107621 | 1 | 153.5 | 4.36E-05 | 0.242328 | ******* | Study 3 | -- | 366 | 146 |
| 13 | NC0041280 | 1 | 161.4 | 0 | -0.02301 | C | Study 1 | CV010 | 223 | 153 |
| 13 | NC0041280 | 1 | 161.4 | 0.007487 | -0.02045 | C | Study 1 | CV085 | 223 | 153 |
| 13 | NC0041280 | 1 | 161.4 | 0.002759 | -0.00882 | C | Study 1 | CV085 | 223 | 153 |
| 13 | NC0042754 | 1 | 164 | 0.028177 | 0.04742 | T | Study 4 | -- | 76 | 1241 |
| 13 | NC0021568 | 1 | 167.1 | 0 | -0.02336 | C | Study 1 | CV010 | 90 | 159 |
| 13 | NC0070702 | 1 | 167.1 | 0.009394 | -0.08811 | C | Study 4 | -- | 1001 | 160 |
| 13 | NC0009626 | 1 | 169.6 | 0 | -0.02442 | C | Study 1 | CV010 | 236 | 162 |
| 14 | NC0105648 | 1 | 172.2 | 0.03034 | -0.00643 | T | Study 1 | CV085 | 264 | 164 |
| 14 | NC0067728 | 1 | 173.7 | 0 | -0.02632 | T | Study 1 | CV010 | 218 | 166 |
| 14 | NC0069344 | 1 | 176.9 | 0 | -0.02588 | A | Study 1 | CV010 | 206 | 169 |
| 14 | NC0027567 | 1 | 179.4 | 9.27E-05 | 0.242128 | G | Study 3 | -- | 79 | 172 |
| 15 | NC0004909 | 1 | 182.1 | 0 | -0.02769 | A | Study 1 | CV010 | 324 | 175 |
| 15 | NC0004909 | 1 | 182.1 | 0.022324 | 0.02151 | A | Study 1 | LH287 | 324 | 175 |
| 15 | NC0005098 | 1 | 183.9 | 0 | -0.02729 | A | Study 1 | CV010 | 133 | 177 |
| 16 | NC0016674 | 1 | 202.2 | 0.0004 | -0.15049 | A | Study 2 | -- | 154 | 1242 |
| 16 | NC0013584 | 1 | 204.4 | 0.035163 | -0.06693 | C | Study 1 | CV120 | 304 | 186 |
| 16 | NC0013584 | 1 | 204.4 | 0.004577 | 0.027157 | T | Study 1 | LH287 | 304 | 186 |
| 17 | NC0015344 | 1 | 221.1 | <.0001 | 0.123021 | G | Study 2 | -- | 420 | 200 |
| 18 | NC0146570 | 1 | 237 | 0.003453 | 0.018264 | T | Study 2 | CV121 | 232 | 202 |
| 18 | NC0110139 | 1 | 237.2 | 0.013037 | 0.02569 | T | Study 1 | -- | 224 | 203 |
| 19 | NC0013490 | 1 | 240.7 | 0.003666 | 0.018036 | T | Study 4 | CV121 | 482 | 207 |
| 19 | NC0030840 | 1 | 245.1 | 0.004279 | 0.018013 | A | Study 1 | CV121 | 413 | 208 |
| 20 | NC0016137 | 1 | 256.3 | 0.032379 | 0.013563 | C | Study 1 | CV121 | 482 | 1243 |

FIGURE 1 CONT.

| QTL | Marker | Chr | pos | Sig | effect | res allele | Mapping Study | Fav. Parent | SNP Position | SEQ ID |
|---|---|---|---|---|---|---|---|---|---|---|
| 21 | NC0015766 | 2 | 7 | 0.003324 | 0.020948 | G | Study 4 | -- | 360 | 215 |
| 22 | NC0009766 | 2 | 10.1 | 0.037837 | 0.04816 | T | Study 4 | -- | 328 | 216 |
| 22 | NC0033786 | 2 | 15.2 | 0.021898 | -0.02638 | A | Study 4 | -- | 108 | 1244 |
| 22 | NC0106678 | 2 | 18.3 | 0.000271 | 0.116208 | G | Study 1 | LH287 | 309 | 220 |
| 22 | NC0106678 | 2 | 18.3 | 0.000271 | 0.116208 | G | Study 1 | LH287 | 309 | 220 |
| 22 | NC0002814 | 2 | 27.9 | 0.000001 | 0.155237 | C | Study 1 | LH287 | 92 | 224 |
| 23 | NC0002616 | 2 | 34 | 0.016239 | 0.074511 | C | Study 1 | LH287 | 53 | 228 |
| 24 | NC0009706 | 2 | 35.9 | 0.014254 | 0.007758 | G | Study 1 | LH287 | 269 | 231 |
| 24 | NC0107479 | 2 | 42.3 | 0.006131 | 0.08519 | A | Study 1 | LH287 | 195 | 232 |
| 25 | NC0109140 | 2 | 44.8 | 0.016804 | -0.01645 | TAAA | Study 1 | CV085 | 578 | 233 |
| 25 | NC0048553 | 2 | 46.8 | 0.004592 | 0.008892 | A | Study 1 | LH287 | 485 | 234 |
| 25 | NC0048553 | 2 | 46.8 | 0.000006 | 0.142232 | A | Study 1 | LH287 | 485 | 234 |
| 25 | NC0048553 | 2 | 46.8 | 0.000006 | 0.142232 | A | Study 1 | LH287 | 485 | 234 |
| 25 | NC0078243 | 2 | 48.8 | 0.028571 | 0.097888 | G | Study 4 | -- | 229 | 235 |
| 25 | NC0078243 | 2 | 48.8 | 0.003324 | -0.01908 | G | Study 1 | CV085 | 229 | 235 |
| 26 | NC0020105 | 2 | 64.6 | 0.00941 | -0.01685 | A | Study 1 | CV085 | 55 | 244 |
| 26 | NC0020105 | 2 | 64.6 | 0.037454 | 0.019556 | G | Study 1 | LH287 | 55 | 244 |
| 26 | NC0080705 | 2 | 68.5 | 0.005854 | 0.00884 | G | Study 1 | LH287 | 281 | 248 |
| 26 | NC0080705 | 2 | 68.5 | 0.022582 | 0.071256 | G | Study 1 | LH287 | 281 | 248 |
| 26 | NC0080705 | 2 | 68.5 | 0.000096 | 0.1266 | C | Study 1 | LH287 | 281 | 248 |
| 27 | NC0032200 | 2 | 71.6 | 0.016486 | 0.022504 | G | Study 1 | LH287 | 318 | 250 |
| 27 | NC0004697 | 2 | 74.8 | <.0001 | 0.304299 | G | Study 2 | -- | 175 | 252 |
| 27 | NC0042242 | 2 | 77 | 0.003374 | 0.097205 | T | Study 1 | LH287 | 75 | 256 |
| 27 | NC0015022 | 2 | 77.3 | 0.004176 | -0.04752 | A | Study 4 | -- | 143 | 257 |
| 27 | NC0035381 | 2 | 79.6 | 0.024821 | 0.007253 | T | Study 1 | LH287 | 80 | 260 |
| 28 | NC0105002 | 2 | 88.6 | 0.048425 | -0.04207 | C | Study 4 | -- | 167 | 265 |
| 28 | NC0108493 | 2 | 88.6 | <.0001 | -0.17752 | A | Study 2 | -- | 304 | 266 |
| 28 | NC0146518 | 2 | 89.4 | 0.003188 | 0.009437 | G | Study 1 | LH287 | 97 | 267 |
| 29 | NC0053463 | 2 | 93.1 | 0.031181 | -0.05564 | A | Study 4 | -- | 461 | 271 |
| 29 | NC0021092 | 2 | 93.4 | 0.01458 | -0.07801 | A | Study 2 | -- | 94 | 273 |
| 29 | NC0021092 | 2 | 93.4 | <.0001 | -0.23525 | A | Study 2 | -- | 94 | 273 |
| 29 | NC0021405 | 2 | 93.4 | 0.0021 | 0.184068 | G | Study 2 | -- | 162 | 1245 |
| 29 | NC0057604 | 2 | 94 | 0.012688 | -0.07582 | CAGG | Study 4 | -- | 412 | 274 |
| 29 | NC0105696 | 2 | 94.3 | 0.02062 | 0.071815 | T | Study 4 | -- | 149 | 278 |

FIGURE 1 CONT.

| QTL | Marker | Chr | pos | Sig | effect | res allele | Mapping Study | Fav. Parent | SNP Position | SEQ ID |
|---|---|---|---|---|---|---|---|---|---|---|
| 29 | NC0146130 | 2 | 94.6 | 0.004449 | 0.091703 | G | Study 4 | -- | 96 | 279 |
| 29 | NC0032601 | 2 | 94.9 | 0.004916 | -0.01262 | T | Study 1 | CV010 | 144 | 282 |
| 29 | NC0108305 | 2 | 97.9 | 0.002427 | 0.113785 | G | Study 4 | -- | 174 | 287 |
| 29 | NC0107911 | 2 | 99.2 | 0.003188 | 0.009437 | T | Study 1 | LH287 | 384 | 289 |
| 29 | NC0107911 | 2 | 99.2 | 0.017596 | 0.023946 | T | Study 1 | LH287 | 384 | 289 |
| 29 | NC0107911 | 2 | 99.2 | 0.018178 | 0.077377 | T | Study 1 | LH287 | 384 | 289 |
| 29 | NC0107911 | 2 | 99.2 | 0.018178 | 0.077377 | T | Study 1 | LH287 | 384 | 289 |
| 30 | NC0108607 | 2 | 102.1 | 0.023127 | -0.00991 | C | Study 1 | CV010 | 562 | 294 |
| 30 | NC0153941 | 2 | 102.1 | 0.015176 | 0.023873 | CTT | Study 1 | LH287 | 1176 | 295 |
| 30 | NC0053097 | 2 | 102.6 | 0.004803 | 0.080678 | T | Study 4 | -- | 335 | 296 |
| 30 | NC0057210 | 2 | 104.1 | 0.013072 | -0.01105 | C | Study 1 | CV010 | 191 | 299 |
| 31 | NC0084632 | 2 | 124.1 | <.0001 | -0.2503 | C | Study 2 | -- | 206 | 1246 |
| 31 | NC0109393 | 2 | 127.1 | 0.021202 | -0.07794 | A | Study 3 | -- | 323 | 317 |
| 31 | NC0040472 | 2 | 128.8 | 0.023017 | -0.00642 | C | Study 1 | CV085 | 102 | 320 |
| 32 | NC0031474 | 2 | 141.4 | 0.012787 | -0.00693 | A | Study 1 | CV085 | 842 | 332 |
| 32 | NC0031474 | 2 | 141.4 | 0.041884 | 0.006559 | A | Study 1 | LH287 | 842 | 332 |
| 32 | NC0002878 | 2 | 145.1 | 0.000253 | -0.05653 | C | Study 4 | -- | 286 | 333 |
| 32 | NC0005088 | 2 | 147.6 | 0.010516 | -0.08747 | T | Study 3 | -- | 110 | 334 |
| 32 | NC0005088 | 2 | 147.6 | 0.047321 | 0.040916 | A | Study 4 | -- | 110 | 334 |
| 33 | NC0085297 | 2 | 150.7 | 6.69E-05 | -0.0763 | G | Study 4 | -- | 207 | 337 |
| 33 | NC0085297 | 2 | 150.7 | 0.0203 | 0.007441 | G | Study 1 | LH287 | 207 | 337 |
| 34 | NC0014467 | 2 | 167.3 | 0.022787 | -0.07608 | AT | Study 3 | -- | 366 | 347 |
| 34 | NC0014467 | 2 | 167.3 | 0.006993 | -0.01788 | AT | Study 1 | CV085 | 366 | 347 |
| 35 | NC0110974 | 2 | 185.5 | 0.02837 | -0.01488 | T | Study 1 | CV085 | 522 | 355 |
| 36 | NC0106389 | 3 | 14.2 | 0.03523 | 0.006226 | A | Study 1 | CV012 | 207 | 362 |
| 36 | NC0008911 | 3 | 19.9 | 0.001193 | 0.103961 | G | Study 1 | LH287 | 205 | 363 |
| 37 | NC0104528 | 3 | 24.6 | 0.006011 | 0.008258 | G | Study 1 | CV012 | 117 | 1247 |
| 38 | NC0048700 | 3 | 31.3 | 0.066464 | -0.00633 | A | Study 1 | CV012 | 85 | 366 |
| 38 | NC0048700 | 3 | 31.3 | 0.004943 | 0.091568 | T | Study 1 | LH287 | 85 | 366 |
| 39 | NC0032137 | 3 | 40.2 | 0.012587 | 0.07729 | * | Study 3 | -- | 216 | 367 |
| 40 | NC0106329 | 3 | 53.9 | 0.025915 | 0.078684 | G | Study 3 | -- | 91 | 370 |
| 40 | NC0106329 | 3 | 53.9 | 0.005581 | 0.028641 | G | Study 1 | LH287 | 91 | 370 |
| 40 | NC0106329 | 3 | 53.9 | 0.048034 | 0.064481 | G | Study 1 | LH287 | 91 | 370 |
| 41 | NC0105291 | 3 | 83.2 | <.0001 | 0.346974 | T | Study 2 | -- | 294 | 381 |

FIGURE 1 CONT.

| QTL | Marker | Chr | pos | Sig | effect | res allele | Mapping Study | Fav. Parent | SNP Position | SEQ ID |
|---|---|---|---|---|---|---|---|---|---|---|
| 41 | NC0106515 | 3 | 83.2 | 0.000943 | 0.03265 | G | Study 1 | LH287 | 184 | 382 |
| 41 | NC0106515 | 3 | 83.2 | <.0001 | -0.13382 | G | Study 2 | -- | 184 | 382 |
| 41 | NC0009468 | 3 | 88 | 0.007021 | -0.10812 | A | Study 4 | -- | 102 | 392 |
| 41 | NC0031647 | 3 | 89.5 | 0.042292 | -0.1009 | C | Study 4 | -- | 899 | 395 |
| 41 | NC0009739 | 3 | 102.2 | 0.004016 | -0.18037 | A | Study 3 | -- | 284 | 409 |
| 42 | NC0104504 | 3 | 104 | 0.0006 | 0.122768 | G | Study 2 | -- | 406 | 411 |
| 42 | NC0013092 | 3 | 105.4 | 0.0013 | -0.13783 | A | Study 2 | -- | 369 | 412 |
| 43 | NC0155775 | 3 | 111.4 | 0.032869 | 0.001744 | G | Study 4 | -- | 162 | 419 |
| 43 | NC0024395 | 3 | 116 | 0.017221 | -0.01632 | C | Study 1 | CV085 | 75 | 422 |
| 43 | NC0079081 | 3 | 117.1 | 0.008699 | 0.02747 | A | Study 1 | LH287 | 78 | 423 |
| 44 | NC0002905 | 3 | 123.9 | 0.018776 | -0.01573 | A | Study 1 | CV085 | 98 | 429 |
| 44 | NC0009173 | 3 | 124.2 | 0.000505 | 0.120634 | C | Study 4 | -- | 101 | 430 |
| 44 | NC0008922 | 3 | 128.2 | 0.028726 | -0.08618 | A | Study 4 | -- | 271 | 433 |
| 45 | NC0034494 | 3 | 141 | 0.008473 | -0.16454 | A | Study 3 | -- | 524 | 438 |
| 45 | NC0041040 | 3 | 145.4 | 0.0005 | -0.12023 | C | Study 2 | -- | 497 | 440 |
| 45 | NC0036694 | 3 | 148.1 | <.0001 | -0.14922 | A | Study 2 | -- | 180 | 1248 |
| 45 | NC0110128 | 3 | 149.5 | 0.030386 | 0.021434 | A | Study 1 | LH287 | 217 | 447 |
| 46 | NC0028736 | 3 | 152.7 | <.0001 | 0.183625 | G | Study 2 | -- | 371 | 1249 |
| 47 | NC0112491 | 3 | 182.9 | 0.019854 | 0.007439 | G | Study 1 | LH287 | 90 | 474 |
| 47 | NC0146534 | 3 | 183.6 | 0.017851 | -0.13867 | C | Study 4 | -- | 91 | 476 |
| 47 | NC0146497 | 3 | 187.4 | 0.0007 | -0.31952 | A | Study 2 | -- | 98 | 479 |
| 47 | NC0155987 | 3 | 187.4 | 0.0014 | -0.29056 | C | Study 2 | -- | 1001 | 480 |
| 47 | NC0155987 | 3 | 187.4 | 0.03179 | 0.123743 | T | Study 4 | -- | 1001 | 480 |
| 47 | NC0143969 | 3 | 187.5 | 0.028218 | -0.11886 | TA | Study 4 | -- | 100 | 482 |
| 47 | NC0143969 | 3 | 187.5 | 0.041455 | 0.063097 | TA | Study 1 | LH287 | 100 | 482 |
| 48 | NC0010232 | 3 | 198.7 | 0.021444 | 0.013076 | T | Study 1 | CV112 | 353 | 486 |
| 49 | NC0003970 | 3 | 208 | 0.004606 | 0.087194 | A | Study 1 | LH287 | 355 | 490 |
| 50 | NC0014041 | 3 | 217.6 | 0.033595 | 0.134315 | C | Study 3 | -- | 244 | 493 |
| 51 | NC0002739 | 4 | 11.8 | 0.027467 | 0.020664 | C | Study 1 | LH287 | 126 | 500 |
| 52 | NC0034462 | 4 | 67.8 | <.0001 | 0.285633 | T | Study 2 | -- | 301 | 1250 |
| 52 | NC0010305 | 4 | 68.4 | 0.033523 | 0.021092 | A | Study 1 | LH287 | 228 | 525 |
| 52 | NC0033483 | 4 | 69.5 | <.0001 | -0.16104 | C | Study 2 | -- | 163 | 530 |
| 53 | NC0108120 | 4 | 71.5 | <.0001 | 0.34256 | T | Study 2 | -- | 401 | 533 |
| 54 | NC0027345 | 4 | 82.5 | 0.0295 | 0 | -- | Study 4 | -- | 237 | 556 |

FIGURE 1 CONT.

| QTL | Marker | Chr | pos | Sig | effect | res allele | Mapping Study | Fav. Parent | SNP Position | SEQ ID |
|---|---|---|---|---|---|---|---|---|---|---|
| 54 | NC0111228 | 4 | 87.9 | <.0001 | -0.23052 | A | Study 2 | -- | 130 | 566 |
| 55 | NC0077408 | 4 | 104.3 | <.0001 | 0.26398 | C | Study 2 | -- | 294 | 582 |
| 55 | NC0003274 | 4 | 104.7 | <.0001 | -0.20119 | A | Study 2 | -- | 269 | 585 |
| 55 | NC0009280 | 4 | 104.7 | <.0001 | -0.36808 | GCA | Study 2 | -- | 105 | 1251 |
| 56 | NC0110078 | 4 | 115.7 | 0.000557 | -0.01966 | C | Study 1 | CV103 | 99 | 589 |
| 57 | NC0156263 | 4 | 121 | 0.036532 | 0.035766 | T | Study 4 | -- | 338 | 593 |
| 57 | NC0156267 | 4 | 121 | 0.02004 | 0.044271 | T | Study 4 | -- | 321 | 594 |
| 58 | NC0071158 | 4 | 136.7 | 0.017298 | -0.00696 | T | Study 1 | CV085 | 775 | 611 |
| 58 | NC0071158 | 4 | 136.7 | 0.04735 | -0.00629 | G | Study 1 | CV012 | 775 | 611 |
| 59 | NC0028162 | 4 | 141.5 | 0.023562 | -0.01486 | C | Study 1 | CV085 | 313 | 1252 |
| 59 | NC0038447 | 4 | 141.8 | 0.000145 | -0.2403 | A | Study 3 | -- | 526 | 618 |
| 59 | NC0009491 | 4 | 144.6 | 0.045352 | -0.00575 | A | Study 1 | CV085 | 236 | 621 |
| 59 | NC0020933 | 4 | 147.5 | 0.0002 | 0.124182 | T | Study 2 | -- | 373 | 623 |
| 60 | NC0034250 | 4 | 156.3 | 0.02512 | -0.00638 | G | Study 1 | CV085 | 70 | 630 |
| 60 | NC0051079 | 4 | 156.4 | 0.031861 | -0.02094 | G | Study 1 | CV056 | 137 | 632 |
| 60 | NC0037601 | 4 | 162.2 | 0.040958 | -0.00658 | C | Study 1 | CV012 | 478 | 637 |
| 60 | NC0037601 | 4 | 162.2 | 0.032058 | -0.00565 | G | Study 1 | CV012 | 478 | 637 |
| 60 | NC0110455 | 4 | 169.4 | <.0001 | 0.557365 | T | Study 2 | -- | 207 | 639 |
| 61 | NC0009066 | 4 | 181 | 0.03472 | -0.13203 | C | Study 3 | -- | 238 | 646 |
| 61 | NC0148181 | 4 | 183 | 0.016474 | 0 | -- | Study 4 | -- | 1001 | 649 |
| 61 | NC0043794 | 4 | 186.2 | 0.01927 | -0.02185 | G | Study 4 | -- | 197 | 650 |
| 62 | NC0024265 | 5 | 1.8 | 0.010069 | -0.07556 | A | Study 1 | CV120 | 137 | 657 |
| 63 | NC0069592 | 5 | 14.8 | 0.008399 | -0.07734 | AT | Study 1 | CV120 | 439 | 665 |
| 63 | NC0069592 | 5 | 14.8 | 0.000277 | -0.00855 | AT | Study 1 | CV012 | 439 | 665 |
| 64 | NC0011193 | 5 | 29.3 | 0.006766 | 0.090706 | T | Study 3 | -- | 82 | 669 |
| 64 | NC0011193 | 5 | 29.3 | 0.004857 | 0.007911 | T | Study 1 | CV012 | 82 | 669 |
| 64 | NC0011193 | 5 | 29.3 | 0.002346 | 0.013382 | T | Study 1 | CV012 | 82 | 669 |
| 65 | NC0153131 | 5 | 34.4 | 0.00531 | -0.00669 | A | Study 2 | -- | 121 | 1253 |
| 66 | NC0109403 | 5 | 46.7 | 0.0002 | -0.11371 | TTC | Study 3 | -- | 523 | 678 |
| 66 | NC0020401 | 5 | 48 | 0.003351 | 0.097653 | T | Study 3 | CV012 | 175 | 1254 |
| 66 | NC0016527 | 5 | 49 | 0.000006 | 0.01988 | T | Study 1 | -- | 351 | 1255 |
| 67 | NC0037588 | 5 | 60.1 | 0.000154 | 0.230456 | ***** | Study 3 | CV012 | 188 | 679 |
| 67 | NC0009668 | 5 | 65.2 | 0 | 0.023591 | G | Study 1 | CV012 | 107 | 688 |
| 67 | NC0111398 | 5 | 67.7 | 0 | 0.025687 | T | Study 1 | CV012 | 171 | 690 |

FIGURE 1 CONT.

| QTL | Marker | Chr | pos | Sig | effect | res allele | Mapping Study | Fav. Parent | SNP Position | SEQ ID |
|---|---|---|---|---|---|---|---|---|---|---|
| 68 | NC0109411 | 5 | 71.9 | 0.020418 | 0.007501 | C | Study 1 | CV012 | 114 | 1256 |
| 68 | NC0004605 | 5 | 78.5 | 0.005653 | -0.07337 | C | Study 4 | -- | 74 | 704 |
| 68 | NC0146415 | 5 | 79.8 | 0.017437 | 0.039447 | G | Study 4 | -- | 336 | 709 |
| 69 | NC0077644 | 5 | 80.4 | 0.013126 | 0.007991 | A | Study 1 | CV012 | 255 | 710 |
| 69 | NC0077644 | 5 | 80.4 | 0 | 0.025703 | A | Study 1 | CV012 | 255 | 710 |
| 69 | NC0078535 | 5 | 83.9 | 6.55E-05 | -0.15465 | A | Study 4 | -- | 104 | 717 |
| 69 | NC0035956 | 5 | 85.1 | 0.014 | 0.103388 | C | Study 4 | -- | 246 | 719 |
| 69 | NC0154498 | 5 | 85.2 | 0.003588 | -0.10151 | C | Study 4 | -- | 84 | 720 |
| 69 | NC0145634 | 5 | 85.4 | 0.013404 | 0.083897 | T | Study 4 | -- | 346 | 1257 |
| 69 | NC0040571 | 5 | 88.4 | 0.032454 | -0.07295 | C | Study 3 | -- | 154 | 721 |
| 69 | NC0040571 | 5 | 88.4 | 0.015832 | 0.007538 | G | Study 1 | CV012 | 154 | 721 |
| 69 | NC0040571 | 5 | 88.4 | 0.000001 | 0.021889 | G | Study 1 | CV012 | 154 | 721 |
| 69 | NC0111999 | 5 | 96.9 | 0.000695 | 0.015356 | G | Study 1 | CV012 | 587 | 726 |
| 70 | NC0018153 | 5 | 97 | 0.0012 | 0.122587 | G | Study 2 | -- | 573 | 727 |
| 70 | NC0033305 | 5 | 98.9 | 0.017419 | 0.006966 | CGTG | Study 1 | CV012 | 173 | 1258 |
| 71 | NC0017678 | 5 | 103.8 | 0.03668 | -0.00762 | A | Study 4 | -- | 171 | 733 |
| 71 | NC0009297 | 5 | 104.1 | 0.014897 | 0.011512 | A | Study 1 | CV012 | 114 | 734 |
| 72 | NC0009434 | 5 | 125.2 | 0.000919 | 0.10147 | G | Study 1 | LH287 | 123 | 746 |
| 73 | NC0036210 | 5 | 145.2 | 0.004297 | 0.028276 | T | Study 1 | LH287 | 43 | 758 |
| 73 | NC0036210 | 5 | 145.2 | 0.01061 | 0.078681 | T | Study 1 | LH287 | 43 | 758 |
| 73 | NC0143380 | 5 | 148.1 | 0.042413 | 0.140185 | G | Study 3 | -- | 324 | 760 |
| 74 | NC0104717 | 5 | 171.2 | 0.005668 | 0.087309 | T | Study 1 | LH287 | 298 | 764 |
| 74 | NC0012417 | 5 | 175.2 | 0.038749 | -0.07645 | G | Study 4 | -- | 137 | 768 |
| 75 | NC0031084 | 5 | 181.5 | 0.024558 | 0.140101 | G | Study 3 | -- | 53 | 773 |
| 75 | NC0031084 | 5 | 181.5 | 0.000669 | 0.101517 | G | Study 1 | LH287 | 53 | 773 |
| 75 | NC0031084 | 5 | 181.5 | <.0001 | 0.138642 | G | Study 2 | -- | 53 | 773 |
| 76 | NC0003284 | 6 | 36.4 | 0.000001 | 0.02288 | C | Study 1 | CV012 | 439 | 1259 |
| 76 | NC0003210 | 6 | 38.4 | 0.03556 | -0.00501 | C | Study 1 | CV012 | 117 | 792 |
| 76 | NC0003210 | 6 | 38.4 | 0.000027 | 0.019043 | C | Study 1 | CV012 | 250 | 793 |
| 76 | NC0000439 | 6 | 39.9 | 0.000175 | 0.016391 | T | Study 1 | CV012 | 235 | 812 |
| 77 | NC0038040 | 6 | 52.1 | 0.003368 | -0.09931 | A | Study 4 | -- | 382 | 821 |
| 77 | NC0004463 | 6 | 56.5 | 0.022561 | -0.02048 | C | Study 1 | CV056 | 263 | 825 |
| 78 | NC0148039 | 6 | 70.2 | 0.003442 | -0.00793 | T | Study 1 | CV085 | 76 | 835 |
| 78 | NC0148039 | 6 | 70.2 | 0.041391 | 0.004797 | T | Study 1 | LH287 | 76 | 835 |

FIGURE 1 CONT.

| QTL | Marker | Chr | pos | Sig | effect | res allele | Mapping Study | Fav. Parent | SNP Position | SEQ ID |
|---|---|---|---|---|---|---|---|---|---|---|
| 78 | NC0003726 | 6 | 78.5 | 0.044783 | -0.01995 | G | Study 1 | CV056 | 69 | 1260 |
| 78 | NC0082021 | 6 | 79.6 | <.0001 | 0.191138 | ...... | Study 2 | --- | 375 | 844 |
| 79 | NC0066737 | 6 | 81.9 | 0.0002 | -0.16091 | A | Study 2 | --- | 281 | 846 |
| 79 | NC0113381 | 6 | 83.8 | 0.016963 | 0.005846 | G | Study 1 | LH287 | 303 | 850 |
| 79 | NC0040364 | 6 | 85.5 | <.0001 | -0.19557 | A | Study 2 | --- | 258 | 854 |
| 80 | NC0019772 | 6 | 92.4 | 0.021285 | -0.00692 | T | Study 1 | CV085 | 323 | 856 |
| 80 | NC0110972 | 6 | 93.2 | 3.81E-05 | 0.078619 | G | Study 4 | --- | 49 | 857 |
| 80 | NC0110972 | 6 | 93.2 | 0.0003 | 0.122193 | G | Study 2 | --- | 49 | 857 |
| 80 | NC0019588 | 6 | 96.7 | 0.0007 | 0.104198 | T | Study 2 | --- | 361 | 858 |
| 80 | NC0019588 | 6 | 96.7 | 0.019767 | -0.00712 | T | Study 1 | CV085 | 361 | 858 |
| 80 | NC0019588 | 6 | 96.7 | 0.004282 | 0.006776 | C | Study 1 | LH287 | 361 | 858 |
| 81 | NC0081445 | 6 | 101.8 | 0.040744 | 0.011875 | C | Study 1 | CV112 | 198 | 1261 |
| 82 | NC0023358 | 6 | 120.8 | 0.038628 | 0.014067 | C | Study 1 | CV121 | 177 | 874 |
| 83 | NC0028185 | 6 | 130.1 | 0.000992 | 0.112587 | G | Study 3 | --- | 523 | 876 |
| 83 | NC0032509 | 6 | 132.9 | 0.038095 | 0.006632 | A | Study 1 | LH287 | 334 | 880 |
| 83 | NC0053636 | 6 | 136 | 0.0001 | 0.161557 | G | Study 2 | --- | 202 | 882 |
| 84 | NC0032370 | 6 | 144.3 | 0.017401 | 0.007586 | G | Study 1 | LH287 | 929 | 885 |
| 85 | NC0143514 | 7 | 29 | 0.029234 | -0.00522 | G | Study 1 | CV012 | 595 | 893 |
| 86 | NC0003924 | 7 | 43.9 | 0.007199 | -0.00646 | C | Study 1 | CV012 | 412 | 897 |
| 87 | NC0070341 | 7 | 51.3 | 0.034908 | -0.00647 | C | Study 4 | --- | 741 | 1262 |
| 88 | NC0030511 | 7 | 62.8 | 0.001613 | -0.00768 | C | Study 1 | CV012 | 352 | 915 |
| 88 | NC0009073 | 7 | 65.9 | 0.04446 | 0.118303 | : | Study 4 | --- | 191 | 926 |
| 89 | NC0145922 | 7 | 80.5 | 0.046336 | -0.00473 | A | Study 1 | CV012 | 451 | 940 |
| 89 | NC0048425 | 7 | 88.3 | 0.042943 | -0.06241 | T | Study 1 | CV120 | 484 | 942 |
| 90 | NC0009240 | 7 | 98.5 | 0.033051 | -0.00692 | A | Study 1 | CV012 | 379 | 949 |
| 91 | NC0016008 | 7 | 104.6 | 0.040964 | -0.00658 | C | Study 1 | CV012 | 133 | 957 |
| 91 | NC0040335 | 7 | 107 | 0.044944 | -0.00644 | A | Study 1 | CV012 | 407 | 963 |
| 92 | NC0009674 | 7 | 112.1 | 0.018441 | -0.04635 | A | Study 4 | --- | 150 | 964 |
| 93 | NC0004953 | 7 | 131.2 | 0.023377 | 0.145395 | T | Study 3 | --- | 154 | 974 |
| 94 | NC0030970 | 7 | 147.7 | 0.02528 | -0.00717 | CTG | Study 1 | CV012 | 351 | 1263 |
| 95 | NC0155475 | 7 | 154.2 | 0.037533 | -0.06182 | T | Study 1 | CV120 | 77 | 981 |
| 95 | NC0155475 | 7 | 154.2 | 0.023125 | -0.00725 | T | Study 1 | CV012 | 77 | 981 |
| 96 | NC0151568 | 7 | 161.1 | 0.013098 | -0.07203 | C | Study 1 | CV120 | 515 | 983 |
| 96 | NC0038499 | 7 | 169.3 | 0.028951 | 0.13796 | G | Study 3 | --- | 597 | 990 |

FIGURE 1 CONT.

| QTL | Marker | Chr | pos | Sig | effect | res allele | Mapping Study | Fav. Parent | SNP Position | SEQ ID |
|---|---|---|---|---|---|---|---|---|---|---|
| 97 | NC0024672 | 8 | 33.6 | 0.011764 | 0.014419 | A | Study 1 | CV112 | 134 | 997 |
| 97 | NC0019198 | 8 | 38.1 | 0.002 | -0.11075 | C | Study 2 | -- | 316 | 999 |
| 97 | NC0038724 | 8 | 39.6 | 0.000847 | 0.105206 | C | Study 3 | -- | 312 | 1000 |
| 98 | NC0104862 | 8 | 70 | 0.003924 | 0.092608 | T | Study 3 | -- | 321 | 1016 |
| 98 | NC0020099 | 8 | 70.5 | 0.0002 | -0.18265 | C | Study 2 | -- | 379 | 1264 |
| 99 | NC0077568 | 8 | 84 | <.0001 | -0.17866 | A | Study 2 | -- | 245 | 1027 |
| 99 | NC0110378 | 8 | 85.5 | 0.00803 | 0.092386 | ******** | Study 3 | -- | 300 | 1265 |
| 100 | NC0058047 | 8 | 96.1 | <.0001 | -0.2066 | A | Study 2 | -- | 158 | 1043 |
| 101 | NC0105835 | 8 | 104 | 0.00689 | 0.086467 | T | Study 3 | -- | 275 | 1049 |
| 102 | NC0010392 | 8 | 115.4 | <.0001 | -0.24695 | A | Study 2 | -- | 496 | 1053 |
| 102 | NC0012656 | 8 | 115.6 | <.0001 | -0.31542 | A | Study 2 | -- | 156 | 1054 |
| 102 | NC0008831 | 8 | 116.3 | 0.0016 | -0.133 | G | Study 2 | -- | 206 | 1056 |
| 103 | NC0008757 | 8 | 156.3 | 0.01196 | -0.07309 | C | Study 4 | -- | 274 | 1075 |
| 103 | NC0008757 | 8 | 156.3 | 0.044648 | -0.12298 | C | Study 3 | -- | 274 | 1075 |
| 104 | NC0030508 | 8 | 8.3 | 0.0005 | -0.10566 | A | Study 2 | -- | 885 | 1266 |
| 104 | NC0054684 | 9 | 8.3 | 0.037993 | -0.00909 | G | Study 1 | CV010 | 467 | 1081 |
| 105 | NC0049557 | 9 | 25.7 | 0.0002 | -0.21727 | A | Study 2 | -- | 464 | 1087 |
| 106 | NC0012830 | 9 | 33.1 | 0.027936 | -0.00966 | A | Study 1 | CV010 | 334 | 1088 |
| 106 | NC0012830 | 9 | 33.1 | 0.00807 | 0.023919 | A | Study 1 | LH287 | 334 | 1088 |
| 106 | NC0012830 | 9 | 33.1 | 0.00367 | 0.08419 | A | Study 1 | LH287 | 334 | 1088 |
| 107 | NC0028095 | 9 | 59.4 | 0.00328 | -0.04071 | C | Study 4 | -- | 116 | 1098 |
| 108 | NC0010643 | 9 | 60.6 | 0.048151 | 0.124326 | G | Study 4 | -- | 184 | 1099 |
| 108 | NC0055759 | 9 | 62.1 | 0.000377 | 0.031296 | T | Study 1 | LH287 | 149 | 1100 |
| 108 | NC0144042 | 9 | 66.5 | <.0001 | -0.2038 | A | Study 2 | -- | 130 | 1104 |
| 108 | NC0004407 | 9 | 67.2 | 0.044305 | 0 | -- | Study 4 | -- | 49 | 1105 |
| 108 | NC0106791 | 9 | 68.5 | 0.045643 | -0.02074 | C | Study 4 | -- | 181 | 1108 |
| 108 | NC0106791 | 9 | 68.5 | <.0001 | -0.2186 | C | Study 2 | -- | 181 | 1108 |
| 108 | NC0110377 | 9 | 68.5 | 0.00518 | 0.055632 | T | Study 4 | -- | 538 | 1110 |
| 109 | NC0148696 | 9 | 73.2 | 0.000779 | 0.030165 | G | Study 1 | LH287 | 140 | 1267 |
| 109 | NC0020048 | 9 | 77.5 | 0.008116 | 0 | -- | Study 4 | -- | 414 | 1115 |
| 110 | NC0002383 | 9 | 83.3 | 0.002997 | 0.090942 | G | Study 1 | LH287 | 63 | 1122 |
| 110 | NC0155793 | 9 | 84.5 | 0.002037 | 0.006672 | T | Study 4 | -- | 129 | 1268 |
| 110 | NC0004123 | 9 | 84.6 | 0.041266 | 0 | -- | Study 4 | -- | 384 | 1131 |
| 110 | NC0013086 | 9 | 87.3 | 0.002474 | 0.028263 | A | Study 1 | LH287 | 343 | 1133 |

FIGURE 1 CONT.

| QTL | Marker | Chr | pos | Sig | effect | res allele | Mapping Study | Fav. Parent | SNP Position | SBQ ID |
|---|---|---|---|---|---|---|---|---|---|---|
| 111 | NC0145318 | 9 | 91 | 0.024601 | -0.01431 | G | Study 1 | CV085 | 451 | 1269 |
| 111 | NC0106442 | 9 | 98.4 | 0.002316 | -0.0415 | A | Study 4 | -- | 172 | 1142 |
| 112 | NC0041196 | 9 | 101.5 | 0.007955 | 0.082532 | G | Study 4 | -- | 835 | 1143 |
| 112 | NC0042348 | 9 | 101.8 | 0.006537 | -0.11937 | A | Study 4 | -- | 103 | 1145 |
| 112 | NC0042348 | 9 | 101.8 | 0.040352 | 0.063111 | A | Study 1 | LH287 | 103 | 1145 |
| 112 | NC0018417 | 9 | 102.1 | 0.002743 | 0.05722 | C | Study 4 | -- | 287 | 1146 |
| 112 | NC0066389 | 9 | 105.5 | 0.010793 | 0.024425 | G | Study 1 | LH287 | 161 | 1148 |
| 112 | NC0066390 | 9 | 105.5 | 0.048326 | -0.055953 | A | Study 4 | -- | 179 | 1149 |
| 113 | NC0110800 | 9 | 117.7 | 0.0002 | 0.237955 | G | Study 2 | -- | 406 | 1270 |
| 114 | NC0039475 | 9 | 122.7 | 0.04715 | 0.066292 | T | Study 3 | -- | 267 | 1159 |
| 115 | NC0020088 | 10 | 8.6 | 0.021211 | 0.021323 | GGAATAACT | Study 1 | LH287 | 267 | 1168 |
| 116 | NC0020502 | 10 | 30.3 | 0.036202 | 0.060641 | G | Study 1 | LH287 | 172 | 1174 |
| 116 | NC0020502 | 10 | 30.3 | 0.036202 | 0.060641 | G | Study 1 | LH287 | 172 | 1174 |
| 117 | NC0154801 | 10 | 40 | 0.038609 | 0.065008 | G | Study 1 | LH287 | 292 | 1271 |
| 117 | NC0154801 | 10 | 40 | 0.038609 | 0.065008 | G | Study 1 | LH287 | 292 | 1271 |
| 117 | NC0143762 | 10 | 46.7 | 0.0019 | 0.192606 | T | Study 2 | -- | 267 | 1184 |
| 117 | NC0147718 | 10 | 47.3 | 0.0002 | 0.262006 | T | Study 2 | -- | 261 | 1186 |
| 118 | NC0005020 | 10 | 52.9 | <.0001 | 0.174463 | T | Study 2 | -- | 311 | 1272 |
| 118 | NC0009350 | 10 | 53 | 0.021122 | 0.13106 | T | Study 3 | -- | 176 | 1196 |
| 119 | NC0009295 | 10 | 61.3 | 0.025103 | 0.129629 | T | Study 3 | -- | 133 | 1204 |
| 120 | NC0027447 | 10 | 75.6 | 0.011531 | 0.041696 | G | Study 4 | -- | 311 | 1212 |
| 120 | NC0030134 | 10 | 79.4 | <.0001 | 0.167583 | ********* | Study 2 | -- | 94 | 1215 |
| 121 | NC0143657 | 10 | 103.5 | 0.046856 | 0.063738 | C | Study 1 | LH287 | 871 | 1273 |
| 121 | NC0143657 | 10 | 103.5 | 0.046856 | 0.063738 | C | Study 1 | LH287 | 871 | 1273 |

FIGURE 1 CONT.

METHODS AND COMPOSITIONS FOR GOSS' WILT RESISTANCE IN CORN

CROSS-REFERENCE TO RELATED APPLICATIONS

This application is a Continuation of U.S. patent application Ser. No. 13/742,042, filed Jan. 15, 2013, which is a Continuation of U.S. patent application Ser. No. 12/201,206, filed Aug. 29, 2008, which claims the benefit of U.S. Provisional Patent Application No. 60/966,706, filed Aug. 29, 2007, each of which are incorporated herein by reference in their entireties.

INCORPORATION OF SEQUENCE LISTING

A sequence listing is contained in the file named "46_25 (54886_003_US).txt" which is 2432172 bytes (measured in MS-Windows) and comprising 1,361 nucleotide sequences, created Jan. 15, 2013, is electronically filed herewith and is incorporated herein by reference in its entirety.

FIELD OF INVENTION

The present invention relates to the field of plant breeding. More specifically, the present invention includes a method of using haploid plants for genetic mapping of traits such as disease resistance. The invention further includes a method for breeding corn plants containing QTL that are associated with Goss' Wilt, a bacterial disease associated with *Clavibacter michiganense* spp.

BACKGROUND OF INVENTION

Goss' Wilt, caused by the bacterial pathogen *Clavibacter michiganensis* subsp. *nebraskensis* (CN), is a disease that causes significant damage to corn crops. Goss' Wilt has been identified throughout the U.S. Corn Belt, primarily in the western regions. Symptoms include leaf freckles which are small dark green to black water soaked spots and vascular wilt which results in loss of yield. Conservation tillage practices can increase pervasiveness because the bacterial pathogen *Clavibacter michiganensis* subsp. *nebraskensis* (CN) can overwinter in debris, particularly stalks, from infected corn plants (Bradbury, J. F. *IMI description of Fungi and Bacteria*, (1998)). A mapping study conducted by Rocheford et al., reported a genomic region on maize Chromosome 4 associated with Goss' Wilt (Rocheford, et al., *Journal of Heredity* 80(5), (1989)). Goss' Wilt is a significant pathogen of corn, and a need exists for development of disease resistant lines.

Breeding for corn plants resistant to Goss' Wilt can be greatly facilitated by the use of marker-assisted selection. Of the classes of genetic markers, single nucleotide polymorphisms (SNPs) have characteristics which make them preferential to other genetic markers in detecting, selecting for, and introgressing disease resistance in a corn plant. SNPs are preferred because technologies are available for automated, high-throughput screening of SNP markers, which can decrease the time to select for and introgress disease resistance in corn plants. Further, SNP markers are ideal because the likelihood that a particular SNP allele is derived from independent origins in the extant population of a particular species is very low. As such, SNP markers are useful for tracking and assisting introgression of disease resistance alleles, particularly in the case of disease resistance haplotypes.

The present invention further provides and includes a method for screening and selecting a corn plant comprising QTL for Goss' Wilt resistance using endemic strains of CN and SNP marker technology.

SUMMARY OF THE INVENTION

Methods for identifying corn plants that comprise alleles of genetic loci associated with Goss' Wilt resistance are provided herein. In certain embodiments, methods of identifying a corn plant comprising at least one allele associated with Goss' Wilt resistance allele in a corn plant comprising: a) genotyping at least one corn plant with at least one nucleic acid marker selected from the group consisting of SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1302, and 1303, and b) selecting at least one corn plant comprising an allele of at least one of the markers that is associated with resistance to Goss' Wilt are provided. In certain embodiments of the methods, the at least one corn plant genotyped in step (a) and/or the at least one corn plant selected in step (b) is a corn plant from a population generated by a cross. In embodiments of the methods where the corn plant from a population generated by a cross, the cross can be effected by mechanical emasculation, chemical sterilization, or genetic sterilization of a pollen acceptor. In certain embodiments of the methods, genotyping is effected in step (a) by determining the allelic state of at least one of the corn genomic DNA markers. In such embodiments of the methods, an allelic state can be determined by single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and/or a Flap Endonuclease-mediated assay(s). In other embodiments of the methods, the selected corn plant(s) of step (b) exhibit at least partial resistance to a Goss' Wilt-inducing bacteria or at least substantial resistance to a Goss' Wilt-inducing bacteria. In certain embodiments of the methods, the nucleic acid marker is selected from the group consisting of SEQ ID NOs: 27, 121, 141, 175, 177, 220, 224, 234, 248, 252, 381, 440, 479, 480, 533, 582, 585, 639, 721, 727, 733, 746, 768, 773, 940, 1053, 1054, 1122, 1186, 1246, 1250, and 1251. Alternatively, the nucleic acid marker can be selected from the group consisting of SEQ ID NOs: 234 and 1250. In embodiments where a population is generated by a cross, the population can be generated by a cross of at least one Goss' Wilt resistant corn plant with at least one Goss' Wilt sensitive corn plant. In certain embodiments of the methods where a population is generated by a cross, the cross can be a back cross of at least one Goss' Wilt resistant corn plant with at least one Goss' Wilt sensitive corn plant to introgress Goss' Wilt resistance into a corn germplasm. In embodiments where the corn plant is from a population, the population can be a segregating population. In certain embodiments of the methods, the population can be a haploid breeding population.

Also provided herein are corn plants obtained by any of the aforementioned methods of identifying corn plants that comprise alleles of genetic loci associated with Goss' Wilt resistance. In certain embodiments, a corn plant obtained by any of these aforementioned methods can comprise at least one allele of a nucleic acid marker selected from the group consisting of SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1302, and 1303, wherein the allele is associated with Goss' Wilt resistance. In certain embodiments, a corn plant obtained by any of these aforementioned methods can comprise at least one allele of a nucleic acid marker is selected from the group consisting of SEQ ID NOs: 27, 121, 141, 175, 177, 220, 224, 234, 248, 252, 381, 440, 479, 480, 533, 582, 585, 639, 721, 727, 733, 746, 768, 773, 940, 1053, 1054, 1122, 1186, 1246, 1250, and 1251, wherein the allele is associated with Goss' Wilt resistance. In certain embodiments, a corn plant obtained by any of these aforementioned methods can comprise at least one allele of a nucleic acid marker is selected from the group consisting of SEQ ID NOs: 234 and 1250, wherein the allele is associated with Goss' Wilt resistance. In certain embodiments, a corn plant obtained by any of these aforementioned methods exhibits at least partial resistance to a Goss' Wilt-inducing bacterium. In certain embodiments, a corn plant obtained by any of these aforementioned methods exhibits at least substantial resistance to a Goss' Wilt-inducing bacterium. In still other embodiments, a corn plant obtained by any of these aforementioned methods can be a haploid corn plant. In certain embodiments, a corn plant obtained by any of the aforementioned methods can comprise at least one transgenic trait. In such embodiments, the transgenic trait can be herbicide tolerance and/or pest resistance. In embodiments where the corn plant obtained is herbicide tolerant, herbicide tolerance can be selected from the group consisting of glyphosate, dicamba, glufosinate, sulfonylurea, bromoxynil and norflurazon herbicide tolerance. In certain embodiments, the nucleic acid marker is present as a single copy in a corn plant obtained by any of these aforementioned methods. In other embodiments, the nucleic acid marker can be present in two copies in a corn plant obtained by any of these aforementioned methods.

Also provided are methods for introgressing a Goss' Wilt resistance QTL into a corn plant. In certain embodiments, methods of introgressing a Goss' Wilt resistance QTL into a corn plant comprising: a) screening a population with at least one nucleic acid marker to determine if one or more corn plants from the population contains a Goss' Wilt resistance QTL, wherein the Goss' Wilt resistance QTL is a QTL selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, and 131 as provided in FIG. 1; and b) selecting from the population at least one corn plant comprising an allele of the marker associated with Goss' Wilt resistance are provided. In certain embodiments of the methods, at least one of the markers is located within 30 cM, 25 cM, 20 cM, 15 cM, or 10 cM of the Goss' Wilt resistance QTL. In other embodiments of the methods, at least one of the markers is located within 5 cM, 2 cM, or 1 cM of the Goss' Wilt resistance QTL. In certain embodiments of the methods, at least one of the markers exhibits an LOD score of greater than 2.0, 2.5, or 3.0 with the Goss' Wilt resistance QTL. In other embodiments of the methods, at least one of the markers exhibits a LOD score of greater than 4.0 with the Goss' Wilt resistance QTL. In certain embodiments of these methods, the nucleic acid marker is selected from the group consisting of SEQ ID NOs: 27, 121, 141, 175, 177, 220, 224, 234, 248, 252, 381, 440, 479, 480, 533, 582, 585, 639, 721, 727, 733, 746, 768, 773, 940, 1053, 1054, 1122, 1186, 1246, 1250, and 1251, wherein the nucleic acid marker is selected from the group consisting of SEQ ID NOs: 234 and 1250. In certain embodiments of the methods, the population is a segregating population.

Also provided herein are corn plants obtained by any of the aforementioned methods of identifying corn plants that comprise a Goss' Wilt resistance QTL. In certain embodiments, a corn plant obtained by any of the aforementioned methods is provided, wherein the corn plant comprises a Goss' Wilt resistance QTL selected from the group consisting of QTL numbers 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, and 131 as provided in FIG. 1. In certain embodiments, a corn plant obtained by any of these aforementioned methods and comprising at least one of the QTL exhibits at least partial resistance to a Goss' Wilt-inducing bacterium. In certain embodiments, a corn plant obtained by any of these aforementioned methods exhibits at least substantial resistance to a Goss' Wilt-inducing bacterium. In still other embodiments, a corn plant obtained by any of these aforementioned methods and comprising at least one of the QTL can be a haploid corn plant. In certain embodiments, a corn plant obtained by any of the aforementioned methods and comprising at least one of the QTL can comprise at least one transgenic trait. In such embodiments, the transgenic trait can be herbicide tolerance and/or pest resistance. In embodiments where the corn plant obtained is herbicide tolerant, herbicide tolerance can be selected from the group consisting of glyphosate, dicamba, glufosinate, sulfonylurea, bromoxynil and norflurazon herbicide tolerance.

Also provided herein are isolated nucleic acid markers for identifying polymorphisms in corn DNA. These isolated nucleic acids can be used in a variety of applications, including but not limited to, the identification of corn plants that comprise alleles of genetic loci associated with Goss' Wilt resistance. In certain embodiments, an isolated nucleic acid molecule for detecting a molecular marker representing a polymorphism in corn DNA, wherein the nucleic acid molecule comprises at least 15 nucleotides that include or are immediately adjacent to the polymorphism, wherein the nucleic acid molecule is at least 90 percent identical to a sequence of the same number of consecutive nucleotides in either strand of DNA that include or are immediately adjacent to the polymorphism, and wherein the molecular marker is selected from the group consisting of SEQ ID NOs: 27, 121, 141, 175, 177, 220, 224, 234, 248, 252, 440, 479, 480, 533, 582, 585, 639, 721, 727, 733, 746, 768, 773, 940, 1053, 1054, 1122, 1186, 1234-1302, and 1303 is provided. In other embodiments, the molecular marker is selected from the group consisting of SEQ ID NOs: 27, 121, 141, 175, 177, 220, 224, 234, 248, 252, 381, 440, 479, 480, 533, 582, 585, 639, 721, 727, 733, 746, 768, 773, 940, 1053, 1054, 1122, 1186, 1246, 1250, and 1251. In still other embodiments, the molecular marker is selected from the group consisting of SEQ ID NOs: 234 and 1250. In certain embodiments, the isolated nucleic acid further comprises a detectable label or provides for incorporation of a detectable label. In such embodiments that comprise or provide for incorporation of a detectable label, the detectable label is selected from the group consisting of an isotope, a fluorophore, an oxidant, a reductant, a nucleotide and a hapten. In certain embodiments, the detectable label is added to the nucleic acid by a chemical reaction or is incorporated by an enzymatic reaction. In certain embodiments, the isolated nucleic acid molecule comprises at least 16 or 17 nucleotides that include or are immediately adjacent to the polymorphism. In other embodiments, the nucleic acid molecule comprises at least 18 nucleotides that include or are immediately adjacent to the polymorphism or comprises at least 20 nucleotides that include or are immediately adjacent to the polymorphism. In certain embodiments, the isolated nucleic acid molecule hybridizes to at least one allele of the molecular marker under stringent hybridization conditions.

BRIEF DESCRIPTION OF THE DRAWINGS

The accompanying drawings, which are incorporated in and form a part of the specification, illustrate the embodiments of the present invention and together with the description, serve to explain the principles of the invention.

In the drawings:

FIG. 1. Displays markers associated with resistance to Goss' Wilt. The symbol "*" represents a single nucleotide deletion.

DETAILED DESCRIPTION OF THE INVENTION

Definitions

The definitions and methods provided herein define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biolgoy of The Cell, 3rd Edition, Garland Publishing, Inc.: New York, 1994; Rieger et al., Glossary of Genetics: Classical and Molecular, 5th Edition, Springer-Verlag: New York, 1991; and Lewin, Genes V, Oxford University Press: New York, 1994. The nomenclature for DNA bases as set forth at 37 CFR §1.822 is used.

As used herein, a "locus" is a fixed position on a chromosome and may represent a single nucleotide, a few nucleotides or a large number of nucleotides in a genomic region.

As used herein, "polymorphism" means the presence of one or more variations of a nucleic acid sequence at one or more loci in a population of one or more individuals. The variation may comprise but is not limited to, one or more base changes, the insertion of one or more nucleotides or the deletion of one or more nucleotides. A polymorphism includes a single nucleotide polymorphism (SNP), a simple sequence repeat (SSR) and indels, which are insertions and deletions. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the later may be associated with rare but important phenotypic variation.

As used herein, "marker" means a detectable characteristic that can be used to discriminate between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics.

As used herein, "genetic marker" means polymorphic nucleic acid sequence or nucleic acid feature. A "polymorphism" is a variation among individuals in sequence, particularly in DNA sequence, or feature, such as a transcriptional profile or methylation pattern. Useful polymorphisms include single nucleotide polymorphisms (SNPs), insertions or deletions in DNA sequence (Indels), simple sequence repeats of DNA sequence (SSRs) a restriction fragment length polymorphism, a haplotype, and a tag SNP. A genetic marker, a gene, a DNA-derived sequence, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, the phrase "immediately adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "immediately adjacent" to the polymorphism.

As used herein, "interrogation position" refers to a physical position on a solid support that can be queried to obtain genotyping data for one or more predetermined genomic polymorphisms.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, the term "single nucleotide polymorphism," also referred to by the abbreviation "SNP," means a polymorphism at a single site wherein said polymorphism constitutes a single base pair change, an insertion of one or more base pairs, or a deletion of one or more base pairs.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, the term "haplotype" means a chromosomal region within a haplotype window defined by at least one polymorphic molecular marker. The unique marker fingerprint combinations in each haplotype window define individual haplotypes for that window. Further, changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in our definition of what constitutes a haplotype so long as the functional integrity of that genomic region is unchanged or improved.

As used herein, the term "haplotype window" means a chromosomal region that is established by statistical analyses known to those of skill in the art and is in linkage disequilibrium. Thus, identity by state between two inbred individuals (or two gametes) at one or more molecular marker loci located within this region is taken as evidence of identity-by-descent of the entire region. Each haplotype window includes at least one polymorphic molecular marker. Haplotype windows can be mapped along each chromosome in the genome. Haplotype windows are not fixed per se and, given the ever-increasing density of molecular markers, this invention anticipates the number and size of haplotype windows to evolve, with the number of windows increasing and their respective sizes decreasing, thus resulting in an ever-increasing degree confidence in ascertaining identity by descent based on the identity by state at the marker loci.

As used herein, a plant referred to as "haploid" has a single set (genome) of chromosomes and the reduced number of chromosomes (n) in the haploid plant is equal to that of the gamete.

As used herein, a plant referred to as "doubled haploid" is developed by doubling the haploid set of chromosomes. A plant or seed that is obtained from a doubled haploid plant that is selfed any number of generations may still be identified as a doubled haploid plant. A doubled haploid plant is considered a homozygous plant. A plant is considered to be doubled haploid if it is fertile, even is the entire vegetative part of the plant does not consist of the cells with the doubled set of chromosomes; that is, a plant will be considered doubled haploid if it contains viable gametes, even if it is chimeric.

As used herein, a plant referred to as "diploid" has two sets (genomes) of chromosomes and the chromosome number (2n) is equal to that of the zygote.

As used herein, the term "plant" includes whole plants, plant organs (i.e., leaves, stems, roots, etc.), seeds, and plant cells and progeny of the same. "Plant cell" includes without limitation seeds, suspension cultures, embryos, meristematic regions, callus tissue, leaves, shoots, gametophytes, sporophytes, pollen, and microspores.

As used herein, a "genetic map" is the ordered list of loci known for a particular genome.

As used herein, "phenotype" means the detectable characteristics of a cell or organism which are a manifestation of gene expression.

As used herein, a "phenotypic marker" refers to a marker that can be used to discriminate phenotypes displayed by organisms.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "quantitative trait locus (QTL)" means a locus that controls to some degree numerically representable traits that are usually continuously distributed.

As used herein, the term "transgene" means nucleic acid molecules in form of DNA, such as cDNA or genomic DNA, and RNA, such as mRNA or microRNA, which may be single or double stranded.

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, the term "tester" means a line used in a testcross with another line wherein the tester and the lines tested are from different germplasm pools. A tester may be isogenic or nonisogenic.

As used herein, "resistance allele" means the isolated nucleic acid sequence that includes the polymorphic allele associated with resistance to the disease or condition of concern.

As used herein, the term "corn" means Zea mays or maize and includes all plant varieties that can be bred with corn, including wild maize species.

As used herein, the term "comprising" means "including but not limited to".

As used herein, an "elite line" is any line that has resulted from breeding and selection for superior agronomic performance.

As used herein, an "inducer" is a line which when crossed with another line promotes the formation of haploid embryos.

As used herein, "haplotype effect estimate" means a predicted effect estimate for a haplotype reflecting association with one or more phenotypic traits, wherein the associations can be made de novo or by leveraging historical haplotype-trait association data.

As used herein, "breeding value" means a calculation based on nucleic acid sequence effect estimates and nucleic acid sequence frequency values, the breeding value of a specific nucleic acid sequence relative to other nucleic acid sequences at the same locus (i.e., haplotype window), or across loci (i.e., haplotype windows), can also be determined. In other words, the change in population mean by fixing said nucleic acid sequence is determined. In addition, in the context of evaluating the effect of substituting a specific region in the genome, either by introgression or a transgenic event, breeding values provide the basis for comparing specific nucleic acid sequences for substitution effects. Also, in hybrid crops, the breeding value of nucleic acid sequences can be calculated in the context of the nucleic acid sequence in the tester used to produce the hybrid.

To the extent to which any of the preceding definitions is inconsistent with definitions provided in any patent or non-patent reference incorporated herein or in any reference found elsewhere, it is understood that the preceding definition will be used herein.

Methods and Compositions for Goss' Wilt Resistance in Corn

The present invention provides a method of using haploid plants to identify genotypes associated with phenotypes of interest wherein the haploid plant is assayed with at least one marker and associating the at least one marker with at least one phenotypic trait. The genotype of interest can then be used to make decisions in a plant breeding program. Such decisions include, but are not limited to, selecting among new breeding populations which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences. Non-limiting examples of germplasm improvement activities include line development, hybrid development, transgenic event selection, making breeding crosses, testing and advancing a plant through self fertilization, using plants for transformation, using plants for candidates for expression constructs, and using plants for mutagenesis.

Non-limiting examples of breeding decisions include progeny selection, parent selection, and recurrent selection for at least one haplotype. In another aspect, breeding decisions relating to development of plants for commercial release comprise advancing plants for testing, advancing plants for purity, purification of sublines during development, inbred development, variety development, and hybrid development. In yet other aspects, breeding decisions and germplasm improvement activities comprise transgenic event selection, making breeding crosses, testing and advancing a plant through self-fertilization, using plants for transformation, using plants for candidates for expression constructs, and using plants for mutagenesis.

In still another embodiment, the present invention acknowledges that preferred haplotypes and QTL identified by the methods presented herein may be advanced as candidate genes for inclusion in expression constructs, i.e., transgenes. Nucleic acids underlying haplotypes or QTL of interest may be expressed in plant cells by operably linking them to a promoter functional in plants. In another aspect, nucleic acids underlying haplotypes or QTL of interest may have their expression modified by double-stranded RNA-mediated gene suppression, also known as RNA interference ("RNAi"), which includes suppression mediated by small interfering RNAs ("siRNA"), trans-acting small interfering RNAs ("ta-siRNA"), or microRNAs ("miRNA"). Examples of RNAi methodology suitable for use in plants are described in detail in U.S. patent application publications 2006/0200878 and 2007/0011775.

Methods are known in the art for assembling and introducing constructs into a cell in such a manner that the nucleic acid molecule for a trait is transcribed into a functional mRNA molecule that is translated and expressed as a protein product. For the practice of the present invention, conventional compositions and methods for preparing and using constructs and host cells are well known to one skilled in the art, see for example, Molecular Cloning: A Laboratory Manual, 3rd Edition Volumes 1, 2, and 3 (2000) J. F. Sambrook, D. W. Russell, and N. Irwin, Cold Spring Harbor Laboratory Press. Methods for making transformation constructs particularly suited to plant transformation include, without limitation, those described in U.S. Pat. Nos. 4,971,908, 4,940,835, 4,769,061 and 4,757,011, all of which are herein incorporated by reference in their entirety. Transformation methods for the introduction of expression units into plants are known in the art and include electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; protoplast transformation as illustrated in U.S. Pat. No. 5,508,184; and Agrobacterium-mediated transformation as illustrated in U.S. Pat. Nos. 5,635,055; 5,824,877; 5,591,616; 5,981,840; and 6,384,301.

The present invention provides Goss' Wilt resistance loci that are located in public bins in the maize genome that were not previously associated with Goss' Wilt resistance.

The present invention provides 130 Goss' Wilt resistance loci that are located in public bins in the maize genome that were not previously associated with Goss' Wilt resistance. QTL were assigned by dividing maize chromosomal regions into 10 cM windows. A total of 131 QTL were identified, with 130 not having been previously reported. SNP markers are also provided for monitoring the introgression of the 131 QTL associated with Goss' Wilt resistance.

In the present invention, Goss' Wilt resistance loci 1-53 and 55-131 have not been previously associated with Goss' Wilt and are provided. SNP markers are also provided for monitoring the introgression of Goss' Wilt resistance. In the present invention, Goss' Wilt resistance loci 1, 2, 3, 4, 5, 6, 7, 8, 9, 10, 11, 12, 13, 14, 15, 16, 17, 18, 19, and 20 are located on Chromosome 1. SNP markers used to monitor the introgression of Goss' Wilt resistance locus 1 include those selected from the group consisting of SEQ ID NOs: 13 and 1274. SNP markers used to monitor the introgression of Goss' Wilt resistance locus 2 included those selected from the group consisting of SEQ ID NOs: 1234 and 19. SNP markers used to monitor the introgression of Goss' Wilt resistance locus 3 include those selected from the group consisting of SEQ ID NOs: 27 and 24. SNP markers used to monitor the introgression of Goss' Wilt resistance locus 4 include SEQ ID NO: 36. SNP markers used to monitor the introgression of Goss' Wilt resistance locus 5 included those selected from the group consisting of SEQ ID NOs: 50 and 53. SNP markers used to monitor the introgression of Goss' Wilt resistance locus 6 include SEQ ID NO: 90. SNP markers used to monitor the introgression of Goss' Wilt resistance locus 7 include those selected from the group consisting of SEQ ID NOs: 94, 95, 97, 1235, 1236, 99, 101, 102, 1237, 106, 1238, 110, 111, and 1239. SNP markers used to monitor the introgression of Goss' Wilt resistance locus 8 include those selected from the group consisting of SEQ ID NOs: 1240, 119, 121, 122, and 124. SNP markers used to monitor the introgression of Goss' Wilt resistance locus 9 include those selected from the group consisting of SEQ ID NOs: 128, 130, 131, and 132. SNP markers used to monitor the introgression of Goss' Wilt resistance locus 10 include those selected from the group consisting of SEQ ID NOs: 136, 138, and 1275. SNP markers used to monitor the introgression of Goss' Wilt resistance locus 11 include SEQ ID NOs: 141. SNP markers used to monitor the introgression of Goss' Wilt resistance locus 12 include SEQ ID NOs: 146. SNP markers used to monitor the introgression of Goss' Wilt resistance locus 13 include those selected from the group consisting of SEQ ID NOs: 153, 1241, 159, 160, 162, and 158. SNP markers used to monitor the introgression of Goss' Wilt resistance locus 14 include those selected from the group consisting of SEQ ID NOs: 164, 166, 169, and 172. SNP markers used to monitor the introgression of Goss' Wilt resistance locus 15 include those selected from the group consisting of SEQ ID NOs: 175 and 177. SNP markers used to monitor the introgression of Goss' Wilt resistance locus 16 include those selected from the group consisting of SEQ ID NOs: 1242 and 186. SNP markers used to monitor the introgression of Goss' Wilt resistance locus 17 include SEQ ID NO: 200. SNP markers used to monitor the introgression of Goss' Wilt resistance locus 18 include those selected from the group consisting of SEQ ID NOs: 202 and 203. SNP markers used to monitor the introgression of Goss' Wilt resistance locus 19 include those selected from the group consisting of SEQ ID NOs: 207 and 208. SNP markers used to monitor the introgression of Goss' Wilt resistance locus 20 include SEQ ID NO: 1243.

In the present invention Goss' Wilt resistance loci 21, 22, 23, 24, 25, 26, 27, 28, 29, 30, 31, 32, 33, 34, 35, and 129 are located on Chromosome 2. SNP markers used to monitor the introgression of Goss' Wilt resistance locus 21 include SEQ ID NO: 215. SNP markers used to monitor the introgression of Goss' Wilt resistance locus 22 include those selected from the group consisting of SEQ ID NOs: 216, 1244, 220, 218, and 1229. SNP markers used to monitor the introgression of Goss' Wilt resistance locus 23 include those selected from the group consisting of SEQ ID NOs: 224. SNP markers used to monitor the introgression of Goss' Wilt resistance locus 24 include those selected from the group consisting of SEQ ID NO: 228, 231, and 1276. SNP markers used to monitor the introgression of Goss' Wilt resistance locus 25 include those selected from the group consisting of SEQ ID NOs: 232, 233, 234, 235, and 236. SNP markers used to monitor the introgression of Goss' Wilt resistance locus 26 include those selected from the group consisting of SEQ ID NOs: 244, 248, and 1277. SNP markers used to monitor the introgression of Goss' Wilt resistance locus 27 include those selected from the group consisting of SEQ ID NOs: 250, 252, 256, 257, 260, 1295, and 0.1278. SNP markers used to monitor the introgression of Goss' Wilt resistance locus 28 include those selected from the group consisting of SEQ ID NOs: 265, 266, and 267. SNP markers used to monitor the introgression of Goss' Wilt resistance locus 29 include those selected from the group consisting of SEQ ID NOs: 271, 273, 1245, 274, 278, 279, 282, 287, 289, and 272. SNP markers used to monitor the introgression of Goss' Wilt resistance locus 30 include those selected from the group consisting of SEQ ID NOs: 294, 295, 296, and 299. SNP markers used to monitor the introgression of Goss' Wilt resistance locus 31 include those selected from the group consisting of SEQ ID NOs: 1246, 317, and 320. SNP markers used to monitor the introgression of Goss' Wilt resistance locus 32 include those selected from the group consisting of SEQ ID NOs: 332, 333, and 334. SNP markers used to monitor the introgression of Goss' Wilt resistance locus 33 include SEQ ID NO: 337. SNP markers used to monitor the introgression of Goss' Wilt resistance locus 34 include SEQ ID NO: 347. SNP markers used to monitor the introgression of Goss' Wilt resistance locus 35 include SEQ ID NO: 355. SNP markers used to monitor the introgression of Goss' Wilt resistance locus 129 include SEQ ID NO: 1294.

In the present invention Goss' Wilt resistance loci 36, 37, 38, 39, 40, 41, 42, 43, 44, 45, 46, 47, 48, 49, 50, 122, and 123 are located on Chromosome 3. SNP markers used to monitor the introgression of Goss' Wilt resistance locus 36 include those selected from the group consisting of SEQ ID NOs: 362 and 363. SNP markers used to monitor the introgression of Goss' Wilt resistance locus 37 include SEQ ID NO: 1247. SNP markers used to monitor the introgression of Goss' Wilt resistance locus 38 include SEQ ID NO: 366. SNP markers used to monitor the introgression of Goss' Wilt resistance locus 39 include those selected from the group consisting of SEQ ID NO: 367, 368, and 1279. SNP markers used to monitor the introgression of Goss' Wilt resistance locus 40 include those selected from the group consisting of SEQ ID NO: 370 and 371. SNP markers used to monitor the introgression of Goss' Wilt resistance locus 41 include those selected from the group consisting of SEQ ID NOs: 381, 382, 392, and 395. SNP markers used to monitor the introgression of Goss' Wilt resistance locus 42 include those selected from the group consisting of SEQ ID NOs: 409, 411, and 412. SNP markers used to monitor the introgression of Goss' Wilt resistance locus 43 include those selected from the group consisting of SEQ ID. NOs: 419, 422, 423, and 1280. SNP markers used to monitor the introgression of Goss' Wilt resistance locus 44 include those selected from the group consisting of SEQ ID NOs: 429, 430, 433 and 1281. SNP markers used to monitor the introgression of Goss' Wilt resistance locus 45 include those selected from the group consisting of SEQ ID NOs: 438, 440, 1248, and 447. SNP markers used to monitor the introgression of Goss' Wilt resistance locus 46 include SEQ ID NO: 1249. SNP markers used to monitor the introgression of Goss' Wilt resistance locus 47 include those selected from the group consisting of SEQ ID NOs: 474, 476, 479, 480, and 482. SNP markers used to monitor the introgression of Goss' Wilt resistance locus 48 include those selected from the group SEQ ID NO: 486. SNP markers used to monitor the introgression of Goss' Wilt resistance locus 49 include SEQ ID NO: 490. SNP markers used to monitor the introgression of Goss' Wilt resistance locus 50 include SEQ ID NO: 493. SNP markers used to monitor the introgression of Goss' Wilt resistance locus 122 include those selected from the group consisting of SEQ ID NOs: 375 and 1296. SNP markers used to monitor the introgression of Goss' Wilt resistance locus 123 include those selected from the group consisting of SEQ ID NOs: 401 and 408.

In the present invention Goss' Wilt resistance loci 51, 52, 53, 54, 55, 56, 57, 58, 59, 60, 61, 124, 125, and 126 are located on Chromosome 4. SNP markers used to monitor the introgression of Goss' Wilt resistance locus 51 include SEQ ID NO: 500. SNP markers used to monitor the introgression of Goss' Wilt resistance locus 52 include those selected from the group consisting of SEQ ID NOs: 1250, 525, and 530. SNP markers used to monitor the introgression of Goss' Wilt resistance locus 53 include SEQ ID NOs: 533. SNP markers used to monitor the introgression of Goss' Wilt resistance locus 54 include those selected from the group consisting of SEQ ID NOs: 556 and 566. SNP markers used to monitor the introgression of Goss' Wilt resistance locus 55 include those selected from the group consisting of SEQ ID NOs: 582, 585, 1251, and 1283. SNP markers used to monitor the introgression of Goss' Wilt resistance locus 56 include those selected from the group consisting of SEQ ID NOs: 589 and 587. SNP markers used to monitor the introgression of Goss' Wilt resistance locus 57 include those selected from the group consisting of SEQ ID NOs: 593, 594, and 599. SNP markers used to monitor the introgression of Goss' Wilt resistance locus 58 include SEQ ID NO: 611, 1297, 1298, and 1284. SNP markers used to monitor the introgression of Goss' Wilt resistance locus 59 include those selected from the group consisting of SEQ ID NOs: 1252, 618, 621, and 623. SNP markers used to monitor the introgression of Goss' Wilt resistance locus 60 include those selected from the group consisting of SEQ ID NOs: 630, 632, 637, 639, and 629. SNP markers used to monitor the introgression of Goss' Wilt resistance locus 61 include those selected from the group consisting of SEQ ID NOs: 646, 649, and 650. SNP markers used to monitor the introgression of Goss' Wilt resistance locus 124 include SEQ ID NO: 498. SNP markers used to monitor the introgression of Goss' Wilt resistance locus 125 include SEQ ID NO: 1282.

In the present invention Goss' Wilt resistance loci 62, 63, 64, 65, 66, 67, 68, 69, 70, 71, 72, 73, 74, 75, and 130 are located on Chromosome 5. SNP markers used to monitor the introgression of Goss' Wilt resistance locus 62 include SEQ ID NO: 657. SNP markers used to monitor the introgression of Goss' Wilt resistance locus 63 include those selected from the group consisting of SEQ ID NOs: 665, 1286, and 1299. SNP markers used to monitor the introgression of Goss' Wilt resistance locus 64 include SEQ ID NO: 669. SNP markers used to monitor the introgression of Goss' Wilt resistance locus 65 include those selected from SEQ ID NO: 1253. SNP markers used to monitor the introgression of Goss' Wilt resistance locus 66 include those selected from the group consisting of SEQ ID NOs: 678, 1254, and 1255. SNP markers used to monitor the introgression of Goss' Wilt resistance locus 67 include those selected from the group consisting of SEQ ID NOs: 679, 688, and 690. SNP markers used to monitor the introgression of Goss' Wilt resistance locus 68 include those selected from the group consisting of SEQ ID NOs: 1256, 704, 709, and 1300. SNP markers used to monitor the introgression of Goss' Wilt resistance locus 69 include those selected from the group consisting of SEQ ID NOs: 710, 717, 719, 720, 1257, and 721. SNP markers used to monitor the introgression of Goss' Wilt resistance locus 70 include those selected from the group SEQ ID NOs: 726, 727, and 1258. SNP markers used to monitor the introgression of Goss' Wilt resistance locus 71 include those selected from the group consisting of SEQ ID NOs: 733 and 734. SNP markers used to monitor the introgression of Goss' Wilt resistance locus 72 include those selected from the group consisting of SEQ ID NOs: 746 and 744. SNP markers used to monitor the introgression of Goss' Wilt resistance locus 73 include those selected from the group consisting of SEQ ID NOs: 758 and 760. SNP markers used to monitor the introgression of Goss' Wilt resistance locus 74 include those selected from the group consisting of SEQ ID NOs: 764, 768, and 1287. SNP markers used to monitor the introgression of Goss' Wilt resistance locus 75 include SEQ ID NO: 773. SNP markers used to monitor the introgression of Goss' Wilt resistance locus 130 include SEQ ID NO: 1301.

In the present invention Goss' Wilt resistance loci 76, 77, 78, 79, 80, 81, 82, 83, and 84 are located on Chromosome 6. SNP markers used to monitor the introgression of Goss' Wilt resistance locus 76 include those selected from the group consisting of SEQ ID NOs: 1259, 792, 793, and 812. SNP markers used to monitor the introgression of Goss' Wilt resistance locus 77 include those selected from the group consisting of SEQ ID NOs: 821 and 825. SNP markers used to monitor the introgression of Goss' Wilt resistance locus 78 include those selected from the group consisting of SEQ ID NOs: 835, 1260, and 844. SNP markers used to monitor the introgression of Goss' Wilt resistance locus 79 include those selected from the group consisting of SEQ ID NOs: 846, 850, and 854. SNP markers used to monitor the introgression of Goss' Wilt resistance locus 80 include those selected from the group consisting of SEQ ID NOs: 856, 857, and 858. SNP markers used to monitor the introgression of Goss' Wilt resistance locus 81 include SEQ ID NO: 1261. SNP markers used to monitor the introgression of Goss' Wilt resistance locus 82 include SEQ ID NO: 874. SNP markers used to monitor the introgression of Goss' Wilt resistance locus 83 include those selected from the group consisting of SEQ ID NOs: 876, 880, and 882. SNP markers used to monitor the introgression of Goss' Wilt resistance locus 84 include SEQ ID NO: 885.

In the present invention Goss' Wilt resistance loci 85, 86, 87, 88, 89, 90, 91, 92, 93, 94, 95, 96, 97, and 127 are located on Chromosome 7. SNP markers used to monitor the introgression of Goss' Wilt resistance locus 85 include SEQ ID NO: 893. SNP markers used to monitor the introgression of Goss' Wilt resistance locus 86 include those selected from the group consisting of SEQ ID NOs: 897 and 896. SNP markers used to monitor the introgression of Goss' Wilt resistance locus 87 include SEQ ID NO: 1262. SNP markers used to monitor the introgression of Goss' Wilt resistance locus 88 include those selected from the group consisting of SEQ ID NOs: 915, 926, and 1288. SNP markers used to monitor the introgression of Goss' Wilt resistance locus 89 include those selected from the group consisting of SEQ ID NOs: 940 and 942. SNP markers used to monitor the introgression of Goss' Wilt resistance locus 90 include those selected from the group consisting of SEQ ID NOs: 949 and 951. SNP markers used to monitor the introgression of Goss' Wilt resistance locus 91 include SEQ ID NO: 957 and 963. SNP markers used to monitor the introgression of Goss' Wilt resistance locus 92 include those selected from the group consisting of SEQ ID NO: 964 and 1289. SNP markers used to monitor the introgression of Goss' Wilt resistance locus 93 include those selected from the group consisting of SEQ ID NO: 974 and 976. SNP markers used to monitor the introgression of Goss' Wilt resistance locus 94 include SEQ ID NO: 1263. SNP markers used to monitor the introgression of Goss' Wilt resistance locus 95 include those selected from the group consisting of SEQ ID NO: 981 and 1291. SNP markers used to monitor the introgression of Goss' Wilt resistance locus 96 include SEQ ID NOs: 983 and 990. SNP markers used to monitor the introgression of Goss' Wilt resistance locus 127 include SEQ ID NO: 1290.

In the present invention Goss' Wilt resistance loci 97, 98, 99, 100, 101, 102, 103, and 131 are located on Chromosome 8. SNP markers used to monitor the introgression of Goss' Wilt resistance locus 97 include those selected from the group consisting of SEQ ID NOs: 997, 999, and 1000. SNP markers used to monitor the introgression of Goss' Wilt resistance locus 98 include those selected from the group consisting of SEQ ID NOs: 1016 and 1264. SNP markers used to monitor the introgression of Goss' Wilt resistance locus 99 include those selected from the group consisting of SEQ ID NOs: 1027, 1265, and 1303. SNP markers used to monitor the introgression of Goss' Wilt resistance locus 100 include SEQ ID NO: 1043. SNP markers used to monitor the introgression of Goss' Wilt resistance locus 101 include SEQ ID NO: 1049. SNP markers used to monitor the introgression of Goss' Wilt resistance locus 102 include SEQ ID NO: 1056. SNP markers used to monitor the introgression of Goss' Wilt resistance locus 103 include SEQ ID NO: 1075. SNP markers used to monitor the introgression of Goss' Wilt resistance locus 131 include SEQ ID NO: 1015.

In the present invention Goss' Wilt resistance loci 104, 105, 106, 107, 108, 109, 110, 111, 112, 113, 114, and 115 are located on Chromosome 9. SNP markers used to monitor the introgression of Goss' Wilt resistance locus 104 include those selected from the group consisting of SEQ ID NOs: 1266 and 1081. SNP markers used to monitor the introgression of Goss' Wilt resistance locus 105 include SEQ ID NO: 1087. SNP markers used to monitor the introgression of Goss' Wilt resistance locus 106 include SEQ ID NO: 1088. SNP markers used to monitor the introgression of Goss' Wilt resistance locus 107 include SEQ ID NO: 1098. SNP markers used to monitor the introgression of Goss' Wilt resistance locus 108 include those selected from the group consisting of SEQ ID NOs: 1099, 1100, 1104, 1105, 1108, 1110, and 1292. SNP markers used to monitor the introgression of Goss' Wilt resistance locus 109 include those selected from the group consisting of SEQ ID NOs: 1267 and 1115. SNP markers used to monitor the introgression of Goss' Wilt resistance locus 110 include those selected from the group consisting of SEQ ID NOs: 1122, 1268, 1131, and 1133. SNP markers used to monitor the introgression of Goss' Wilt resistance locus 111 include those selected from the group consisting of SEQ ID NOs: 1269 and 1142. SNP markers used to monitor the introgression of Goss' Wilt resistance locus 112 include those selected from the group consisting of SEQ ID NOs: 1143, 1145, 1146, 1148, and 1149. SNP markers used to monitor the introgression of Goss' Wilt resistance locus 113 include SEQ ID NO: 1270. SNP markers used to monitor the introgression of Goss' Wilt resistance locus 114 include SEQ ID NO: 1159.

In the present invention Goss' Wilt resistance loci 115, 116, 117, 118, 119, 120, 121, and 122 are located on Chromosome 10. SNP markers used to monitor the introgression of Goss' Wilt resistance locus 115 include SEQ ID NO: 1168. SNP markers used to monitor the introgression of Goss' Wilt resistance locus 116 include SEQ ID NO: 1174. SNP markers used to monitor the introgression of Goss' Wilt resistance locus 117 include those selected from the group consisting of SEQ ID NOs: 1271, 1184, and 1186. SNP markers used to monitor the introgression of Goss' Wilt resistance locus 118 include those selected from the group consisting of SEQ ID NO: 1272 and 1196. SNP markers used to monitor the introgression of Goss' Wilt resistance locus 119 include SEQ ID NO: 1204. SNP markers used to monitor the introgression of Goss' Wilt resistance locus 120 include those selected from the group consisting of SEQ ID NOs: 1212 and 1215. SNP markers used to monitor the introgression of Goss' Wilt resistance locus 121 include SEQ ID NO: 1273. SNP markers used to monitor the introgression of Goss' Wilt resistance locus 128 include SEQ ID NO: 1293.

Exemplary marker assays for screening for Goss' Wilt resistance loci are provided in Tables 3, 4, and 5. Illustrative Goss' Wilt resistance locus 87 SNP marker DNA sequence SEQ ID NO: 896 can be amplified using the primers indicated as SEQ ID NOs: 1332 through 1333 and detected with probes indicated as SEQ ID NOs: 1334 through 1335. Illustrative Goss' Wilt resistance locus 91 SNP marker DNA sequence SEQ ID NO: 951 can be amplified using the primers indicated as SEQ ID NOs: 1336 through 1337 and detected with probes indicated as SEQ ID NOs: 1338 through 1339. Illustrative Goss' Wilt resistance locus 72 SNP marker DNA sequence SEQ ID NO: 733 can be amplified using the primers indicated as SEQ ID NOs: 1340 through 1341 and detected with probes indicated as SEQ ID NOs: 1342 through 1343. Illustrative Goss' Wilt resistance locus 109 SNP marker DNA sequence SEQ ID NO: 1098 can be amplified using the primers indicated as SEQ ID NOs: 1344 through 1345 and detected with probes indicated as SEQ ID NOs: 1346 through 1347. Illustrative oligonucleotide hybridization probes for Goss' Wilt resistance locus 87 SNP marker DNA sequence SEQ ID NO: 896 are provided as SEQ ID NO: 1348 and SEQ ID NO 1349. Illustrative oligonucleotide hybridization probes for Goss' Wilt resistance locus 91 SNP marker DNA sequence SEQ ID NO: 951 are provided as SEQ ID NO: 1350 and SEQ ID NO 1351. Illustrative oligonucleotide hybridization probes for Goss' Wilt resistance locus 72 SNP marker DNA sequence SEQ ID NO: 733 are provided as SEQ ID NO: 1352 and SEQ ID NO 1353. Illustrative oligonucleotide hybridization probes for Goss' Wilt resistance locus 109 SNP marker DNA sequence SEQ ID NO: 1098 are provided as SEQ ID NO: 1354 and SEQ ID NO 1355. An illustrative probe for single base extension assays for Goss' Wilt resistance locus 87 SNP marker DNA sequence SEQ ID NO: 896 is provided as SEQ ID NO: 1356. An illustrative probe for single base extension assays for Goss' Wilt resistance locus 91 SNP marker DNA sequence SEQ ID NO: 951 is provided as SEQ ID NO: 1357. An illustrative probe for single base extension assays for Goss' Wilt resistance locus 72 SNP marker DNA sequence SEQ ID NO: 733 is provided as SEQ ID NO: 1358. An illustrative probe for single base extension assays for Goss' Wilt resistance locus 109 SNP marker DNA sequence SEQ ID NO: 1098 is provided as SEQ ID NO: 1359.

As used herein, Goss' Wilt refers to any Goss' Wilt variant or isolate. A corn plant of the present invention can be resistant to one or more bacteria capable of causing or inducing Goss' Wilt. In one aspect, the present invention provides plants resistant to Goss' Wilt as well as methods and compositions for screening corn plants for resistance or susceptibility to Goss' Wilt, caused by the genus *Clavibacter*. In a preferred aspect, the present invention provides methods and compositions for screening corn plants for resistance or susceptibility to *Clavibacter michiganense* spp.

In an aspect, the plant is selected from the genus *Zea*. In another aspect, the plant is selected from the species *Zea mays*. In a further aspect, the plant is selected from the subspecies *Zea mays* L. ssp. *mays*. In an additional aspect, the plant is selected from the group *Zea mays* L. subsp. *mays* Indentata, otherwise known as dent corn. In another aspect, the plant is selected from the group *Zea mays* L. subsp. *mays* Indurata, otherwise known as flint corn. In an aspect, the plant is selected from the group *Zea mays* L. subsp. *mays* Saccharata, otherwise known as sweet corn. In another aspect, the plant is selected from the group *Zea mays* L. subsp. *mays* Amylacea, otherwise known as flour corn. In a further aspect, the plant is selected from the group Zea mays L. subsp. mays Everta, otherwise known as pop corn. Zea plants include hybrids, inbreds, partial inbreds, or members of defined or undefined populations.

Plants of the present invention can be a corn plant that is very resistant, resistant, substantially resistant, mid-resistant, comparatively resistant, partially resistant, mid-susceptible, or susceptible.

In a preferred aspect, the present invention provides a corn plant to be assayed for resistance or susceptibility to Goss' Wilt by any method to determine whether a corn plant is very resistant, resistant, substantially resistant, mid-resistant, comparatively resistant, partially resistant, mid-susceptible, or susceptible.

Phenotyping for Goss' Wilt is based on visually screening plants to determine percentage of infected leaf area. The percentage of leaf area infected is used to rate plants on a scale of 1 (very resistant) to 9 (susceptible).

A disease resistance QTL of the present invention may be introduced into an elite corn inbred line.

In another aspect, the corn plant can show a comparative resistance compared to a non-resistant control corn plant. In this aspect, a control corn plant will preferably be genetically similar except for the Goss' Wilt resistant allele or alleles in question. Such plants can be grown under similar conditions with equivalent or near equivalent exposure to the pathogen. In this aspect, the resistant plant or plants has less than 25%, 15%, 10%, 5%, 2% or 1% of leaf area infected.

A disease resistance QTL of the present invention may be introduced into an elite corn inbred line. An "elite line" is any line that has resulted from breeding and selection for superior agronomic performance.

A Goss' Wilt resistance QTL of the present invention may also be introduced into an elite corn plant comprising one or more transgenes conferring herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in corn.

A disease resistant QTL allele or alleles can be introduced from any plant that contains that allele (donor) to any recipient corn plant. In one aspect, the recipient corn plant can contain additional Goss' Wilt resistant loci. In another aspect, the recipient corn plant can contain a transgene. In another aspect, while maintaining the introduced QTL, the genetic contribution of the plant providing the disease resistant QTL can be reduced by back-crossing or other suitable approaches. In one aspect, the nuclear genetic material derived from the donor material in the corn plant can be less than or about 50%, less than or about 25%, less than or about 13%, less than or about 5%, 3%, 2% or 1%, but that genetic material contains the Goss' Wilt resistant locus or loci of interest.

It is further understood that a corn plant of the present invention may exhibit the characteristics of any relative maturity group. In an aspect, the maturity group is selected from the group consisting of RM90-95, RM 95-100, RM 100-105, RM 105-110, RM 110-115, and RM 115-120.

The present invention also includes a method of introgressing an allele into a corn plant comprising: (A) crossing at least one Goss' Wilt resistant corn plant with at least one Goss' Wilt sensitive corn plant in order to form a segregating population; (B) screening the segregating population with one or more nucleic acid markers to determine if one or more corn plants from the segregating population contains a Goss' Wilt resistant allele, wherein the Goss' Wilt resistant allele is an allele selected from the group consisting of Goss' Wilt resistant locus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 132, 124, 125, 126, 127, 128, 129, 130, and Goss' Wilt resistant locus 131.

The present invention includes isolated nucleic acid molecules. Such molecules include those nucleic acid molecules capable of detecting a polymorphism genetically or physically linked to a Goss' Wilt locus. Such molecules can be referred to as markers. Additional markers can be obtained that are linked to Goss' Wilt resistance locus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, and Goss' Wilt resistant locus 131 by available techniques. In one aspect, the nucleic acid molecule is capable of detecting the presence or absence of a marker located less than 30, 20, 10, 5, 2, or 1 centimorgans from a Goss' Wilt resistance locus. In another aspect, a marker exhibits a LOD score of 2 or greater, 3 or greater, or 4 or greater with Goss' Wilt, measuring using Qgene Version 2.23 (1996) and default parameters. In another aspect, the nucleic acid molecule is capable of detecting a marker in a locus selected from the group Goss' Wilt resistance locus 1 through resistance locus 131. In a further aspect, a nucleic acid molecule is selected from the group consisting of SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1303, 1332-1359 fragments thereof, complements thereof, and nucleic acid molecules capable of specifically hybridizing to one or more of these nucleic acid molecules.

In a preferred aspect, a nucleic acid molecule of the present invention includes those that will specifically hybridize to one or more of the nucleic acid molecules set forth in SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1303, 1332-1359 or complements thereof or fragments of either under moderately stringent conditions, for example at about 2.0×SSC and about 65° C. In a particularly preferred aspect, a nucleic acid of the present invention will specifically hybridize to one or more of the nucleic acid molecules set forth in SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1303, 1332-1359 or complements or fragments of either under high stringency conditions. In one aspect of the present invention, a preferred marker nucleic acid molecule of the present invention has the nucleic acid sequence set forth in SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1303, 1332-1359 or complements thereof or fragments of either. In another aspect of the present invention, a preferred marker nucleic acid molecule of the present invention shares between 80% and 100% or 90% and 100% sequence identity with the nucleic acid sequences set forth in SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1303, 1332-1359 or complements thereof or fragments of either. In a further aspect of the present invention, a preferred marker nucleic acid molecule of the present invention shares between 95% and 100% sequence identity with the sequences set forth in SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1303, 1332-1359 or complements thereof or fragments of either. In a more preferred aspect of the present invention, a preferred marker nucleic acid molecule of the present invention shares between 98% and 100% sequence identity with the nucleic acid sequence set forth in SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1303, 1332-1359 or complement thereof or fragments of either.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules are exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual*, 2nd Edition, Cold Spring Harbor Press, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa 1984 Nucl. Acids Res. 12:203-213; and Wetmur et al., 1968 J. Mol. Biol. 31:349-370. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments.

A fragment of a nucleic acid molecule provided herein can be of any size. Fragments provided herein include, but are not limited to, fragments of nucleic acid sequences set forth in SEQ ID NOs: 13, 19, 24, 27, 36, 50, 53, 90, 94, 95, 97, 99, 101, 102, 106, 110, 111, 119, 121, 122, 124, 128, 130-132, 136, 138, 141, 146, 153, 158-160, 162, 164, 166, 169, 172, 175, 177, 186, 200, 202, 203, 207, 208, 215, 216, 218, 220, 224, 228, 231-236, 244, 248, 250, 252, 256, 257, 260, 265-267, 271-274, 278, 279, 282, 287, 289, 294-296, 299, 317, 320, 332-334, 337, 347, 355, 362, 363, 366-368, 370, 371, 375, 381, 382, 392, 395, 401, 408, 409, 411, 412, 422, 423, 429, 430, 433, 438, 440, 447, 474, 476, 479, 480, 482, 486, 490, 493, 498, 500, 525, 530, 533, 556, 566, 582, 585, 587, 589, 593, 594, 599, 611, 618, 621, 623, 629, 630, 632, 637, 639, 646, 649, 650, 657, 665, 669, 678, 679, 688, 690, 704, 709, 710, 717, 719-721, 726, 727, 733, 734, 744, 746, 758, 760, 764, 768, 773, 792, 793, 812, 821, 825, 835, 844, 846, 850, 854, 856-858, 874, 876, 880, 882, 885, 893, 896, 897, 915, 926, 940, 942, 949, 951, 957, 963, 964, 974, 976, 981, 983, 990, 997, 999, 1000, 1015, 1016, 1027, 1043, 1049, 1053, 1054, 1056, 1075, 1081, 1087, 1088, 1098-1100, 1104, 1105, 1108, 1110, 1115, 1122, 1131, 1133, 1142, 1143, 1145, 1146, 1148, 1149, 1159, 1168, 1174, 1184, 1186, 1196, 1204, 1212, 1215, 1229, 1234-1303, 1332-1359 and complements thereof. In one aspect, a fragment of a nucleic acid molecule can be 15 to 25, 15 to 30, 15 to 40, 15 to 50, 15 to 100, 20 to 25, 20 to 30, 20 to 40, 20 to 50, 20 to 100, 25 to 30, 25 to 40, 25 to 50, 25 to 100, 30 to 40, 30 to 50, or 30 to 100 nucleotides in length. In another aspect, the fragment can be greater than 10, 15, 20, 25, 30, 35, 40, 50, 100, or 250 nucleotides in length.

Additional genetic markers can be used to select plants with an allele of a QTL associated with Goss' Wilt resistance. Examples of public marker databases include, but are not limited to, the Maize Genome Database located on the world wide web at maizegdb.org, the MaizeSeq database located on the world wide web at maizseq.org, the Panzea maize marker and map database located on the world wide web at panzea.org, and the MAGI database located on the world wide web at plantgenomics.iastate.edu/maize.

Marker Technology

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers, such as single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with alleles of a QTL of the present invention can be utilized.

In one embodiment, nucleic acid-based analyses for the presence or absence of the genetic polymorphism can be used for the selection of seeds in a breeding population. A wide variety of genetic markers for the analysis of genetic polymorphisms are available and known to those of skill in the art. The analysis may be used to select for genes, QTL, alleles, or genomic regions (haplotypes) that comprise or are linked to a genetic marker.

Herein, nucleic acid analysis methods are known in the art and include, but are not limited to, PCR-based detection methods (for example, TaqMan assays), microarray methods, and nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al., 1986 Cold Spring Harbor Symp. Quant. Biol. 51:263-273; European Patent 50,424; European Patent 84,796; European Patent 258,017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form.

Polymorphisms in DNA sequences can be detected or typed by a variety of effective methods well known in the art including, but not limited to, those disclosed in U.S. Pat. Nos. 5,468,613 and 5,217,863; 5,210,015; 5,876,930; 6,030,787; 6,004,744; 6,013,431; 5,595,890; 5,762,876; 5,945,283; 5,468,613; 6,090,558; 5,800,944; and 5,616,464, all of which are incorporated herein by reference in their entireties. However, the compositions and methods of this invention can be used in conjunction with any polymorphism typing method to type polymorphisms in corn genomic DNA samples. These corn genomic DNA samples used include but are not limited to, corn genomic DNA isolated directly from a corn plant, cloned corn genomic DNA, or amplified corn genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464 employing at least one pair of probes having sequences homologous to adjacent portions of the target nucleic acid sequence and having side chains which non-covalently bind to form a stem upon base pairing of said probes to said target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is immediately adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of corn genomic DNA which flanks a region containing the polymorphism to be assayed. Following amplification of the region of the corn genome containing the polymorphism, the PCR product is mixed with the third oligonucleotide (called an extension primer) which is designed to hybridize to the amplified DNA immediately adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In a preferred method for detecting polymorphisms, SNPs and Indels can be detected by methods disclosed in U.S. Pat. Nos. 5,210,015; 5,876,930; and 6,030,787 in which an oligonucleotide probe having a 5'fluorescent reporter dye and a 3'quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

Marker-Trait Associations

For the purpose of QTL mapping, the markers included should be diagnostic of origin in order for inferences to be made about subsequent populations. SNP markers are ideal for mapping because the likelihood that a particular SNP allele is derived from independent origins in the extant populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander et al., (Lander et al., 1989 Genetics, 121:185-199), and the interval mapping, based on maximum likelihood methods described therein, and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, XXell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al., (1989), and further described by Ards and Moreno-Gonzalez, Plant Breeding, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al., 1995 Genetics, 139:1421-1428). Multiple regression methods or models can also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al. (Jansen et al., 1994 Genetics, 136:1447-1455) and Zeng (Zeng 1994 Genetics 136: 1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al., 1995 Theor. Appl. Genet. 91:33-3).

Selection of appropriate mapping populations is important to map construction. The choice of an appropriate mapping population depends on the type of marker systems employed (Tanksley et al., *Molecular mapping in plant chromosomes. chromosome structure and function: Impact of new concepts* J. P. Gustafson and R. Appels (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted× adapted).

An $F_2$ population is the first generation of selfing. Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., 1992 Proc. Natl. Acad. Sci. (USA) 89:1477-1481). However, as the distance between markers becomes larger (i.e., loci become more independent), the information in RIL populations decreases dramatically.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., 1992). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al., 1991 Proc. Natl. Acad. Sci. (U.S.A.) 88:9828-9832). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

Marker-Assisted Breeding

Further, the present invention contemplates that preferred haploid plants comprising at least one genotype of interest are identified using the methods disclosed in U.S. Patent Application Ser. No. 60/837,864, which is incorporated herein by reference in its entirety, wherein a genotype of interest may correspond to a QTL or haplotype and is associated with at least one phenotype of interest. The methods include association of at least one haplotype with at least one phenotype, wherein the association is represented by a numerical value and the numerical value is used in the decision-making of a breeding program. Non-limiting examples of numerical values include haplotype effect estimates, haplotype frequencies, and breeding values. In the present invention, it is particularly useful to identify haploid plants of interest based on at least one genotype, such that only those lines undergo doubling, which saves resources. Resulting doubled haploid plants comprising at least one genotype of interest are then advanced in a breeding program for use in activities related to germplasm improvement.

In the present invention, haplotypes are defined on the basis of one or more polymorphic markers within a given haplotype window, with haplotype windows being distributed throughout the crop's genome. In another aspect, de novo and/or historical marker-phenotype association data are leveraged to infer haplotype effect estimates for one or more phenotypes for one or more of the haplotypes for a crop. Haplotype effect estimates enable one skilled in the art to make breeding decisions by comparing haplotype effect estimates for two or more haplotypes. Polymorphic markers, and respective map positions, of the present invention are provided in U.S. Patent Applications 2005/0204780, 2005/0216545, 2005/0218305, and Ser. No. 11/504,538, which are incorporated herein by reference in their entirety.

In yet another aspect, haplotype effect estimates are coupled with haplotype frequency values to calculate a haplotype breeding value of a specific haplotype relative to other haplotypes at the same haplotype window, or across haplotype windows, for one or more phenotypic traits. In other words, the change in population mean by fixing the haplotype is determined. In still another aspect, in the context of evaluating the effect of substituting a specific region in the genome, either by introgression or a transgenic event, haplotype breeding values are used as a basis in comparing haplotypes for substitution effects. Further, in hybrid crops, the breeding value of haplotypes is calculated in the context of at least one haplotype in a tester used to produce a hybrid. Once the value of haplotypes at a given haplotype window are determined and high density fingerprinting information is available on specific varieties or lines, selection can be applied to these genomic regions using at least one marker in the at least one haplotype.

In the present invention, selection can be applied at one or more stages of a breeding program:

a) Among genetically distinct populations, herein defined as "breeding populations," as a pre-selection method to increase the selection index and drive the frequency of favorable haplotypes among breeding populations, wherein preselection is defined as selection among populations based on at least one haplotype for use as parents in breeding crosses, and leveraging of marker-trait association identified in previous breeding crosses.

b) Among segregating progeny from a breeding population, to increase the frequency of the favorable haplotypes for the purpose of line or variety development.

c) Among segregating progeny from a breeding population, to increase the frequency of the favorable haplotypes prior to QTL mapping within this breeding population.

d) For hybrid crops, among parental lines from different heterotic groups to predict the performance potential of different hybrids.

In the present invention, it is contemplated that methods of determine associations between genotype and phenotype in haploid plants can be performed based on haplotypes, versus markers alone (Fan et al., 2006 Genetics). A haplotype is a segment of DNA in the genome of an organism that is assumed to be identical by descent for different individuals when the knowledge of identity by state at one or more loci is the same in the different individuals, and that the regional amount of linkage disequilibrium in the vicinity of that segment on the physical or genetic map is high. A haplotype can be tracked through populations and its statistical association with a given trait can be analyzed. By searching the target space for a QTL association across multiple QTL mapping populations that have parental lines with genomic regions that are identical by descent, the effective population size associated with QTL mapping is increased. The increased sample size results in more recombinant progeny which increases the precision of estimating the QTL position.

Thus, a haplotype association study allows one to define the frequency and the type of the ancestral carrier haplotype. An "association study" is a genetic experiment where one tests the level of departure from randomness between the segregation of alleles at one or more marker loci and the value of individual phenotype for one or more traits. Association studies can be done on quantitative or categorical traits, accounting or not for population structure and/or stratification. In the present invention, associations between haplotypes and phenotypes for the determination of "haplotype effect estimates" can be conducted de novo, using mapping populations for the evaluation of one or more phenotypes, or using historical genotype and phenotype data.

A haplotype analysis is important in that it increases the statistical power of an analysis involving individual biallelic markers. In a first stage of a haplotype frequency analysis, the frequency of the possible haplotypes based on various combinations of the identified biallelic markers of the invention is determined. The haplotype frequency is then compared for distinct populations and a reference population. In general, any method known in the art to test whether a trait and a genotype show a statistically significant correlation may be used.

Methods for determining the statistical significance of a correlation between a phenotype and a genotype, in this case a haplotype, may be determined by any statistical test known in the art and with any accepted threshold of statistical significance being required. The application of particular methods and thresholds of significance are well within the skill of the ordinary practitioner of the art.

To estimate the frequency of a haplotype, the base reference germplasm has to be defined (collection of elite inbred lines, population of random mating individuals, etc.) and a representative sample (or the entire population) has to be genotyped. For example, in one aspect, haplotype frequency is determined by simple counting if considering a set of inbred individuals. In another aspect, estimation methods that employ computing techniques like the Expectation/Maximization (EM) algorithm are required if individuals genotyped are heterozygous at more than one locus in the segment and linkage phase is unknown (Excoffier et al., 1995 Mol. Biol. Evol. 12: 921-927; Li et al., 2002 Biostatistics). Preferably, a method based on the EM algorithm (Dempster et al., 1977 J. R. Stat. Soc. Ser. B 39:1-38) leading to maximum-likelihood estimates of haplotype frequencies under the assumption of Hardy-Weinberg proportions (random mating) is used (Excoffier et al., 1995 Mol. Biol. Evol. 12: 921-927). Alternative approaches are known in the art that for association studies: genome-wide association studies, candidate region association studies and candidate gene association studies (Li et al., 2006 BMC Bioinformatics 7:258). The polymorphic markers of the present invention may be incorporated in any map of genetic markers of a plant genome in order to perform genome-wide association studies.

The present invention comprises methods to detect an association between at least one haplotype in a haploid crop plant and a preferred trait, including a transgene, or a multiple trait index and calculate a haplotype effect estimate based on this association. In one aspect, the calculated haplotype effect estimates are used to make decisions in a breeding program. In another aspect, the calculated haplotype effect estimates are used in conjunction with the frequency of the at least one haplotype to calculate a haplotype breeding value that will be used to make decisions in a breeding program. A multiple trait index (MTI) is a numerical entity that is calculated through the combination of single trait values in a formula. Most often calculated as a linear combination of traits or normalized derivations of traits, it can also be the result of more sophisticated calculations (for example, use of ratios between traits). This MTI is used in genetic analysis as if it were a trait.

Any given chromosome segment can be represented in a given population by a number of haplotypes that can vary from 1 (region is fixed), to the size of the population times the ploidy level of that species (2 in a diploid species), in a population in which every chromosome has a different haplotype. Identity-by-descent among haplotype carried by multiple individuals in a non-fixed population will result in an intermediate number of haplotype and possibly a differing frequency among the different haplotypes. New haplotypes may arise through recombination at meiosis between existing haplotypes in heterozygous progenitors. The frequency of each haplotype may be estimated by several means known to one versed in the art (e.g. by direct counting, or by using an EM algorithm). Let us assume that "k" different haplotypes, identified as "$h_i$" (i=1, . . . , k), are known, that their frequency in the population is "$f_i$" (i=1, . . . , k), and for each of these haplotypes we have an effect estimate "$Est_i$" (i=1, . . . , k). If we call the "haplotype breeding value" ($BV_i$) the effect on that population of fixing that haplotype, then this breeding value corresponds to the change in mean for the trait(s) of interest of that population between its original state of haplotype distribution at the window and a final state at which haplotype "$h_i$" encounters itself at a frequency of 100%.

The haplotype breeding value of $h_i$ in this population is calculated as:

$$BV_i = Est_i - \sum_{i=1}^{k} Est_i f_i$$

One skilled in the art will recognize that haplotypes that are rare in the population in which effects are estimated tend to be less precisely estimated, this difference of confidence may lead to adjustment in the calculation. For example one can ignore the effects of rare haplotypes, by calculating breeding value of better known haplotype after adjusting the frequency of these (by dividing it by the sum of frequency of the better known haplotypes). One could also provide confidence intervals for the breeding value of each haplotypes.

The present invention anticipates that any particular haplotype breeding value will change according to the population for which it is calculated, as a function of difference of haplotype frequencies. The term "population" will thus assume different meanings, below are two examples of special cases. In one aspect, a population is a single inbred in which one intends to replace its current haplotype $h_j$ by a new haplotype $h_i$, in this case $BV_i = Est_i - Est_j$. In another aspect, a "population" is a F2 population in which the two parental haplotype $h_i$ and $h_j$ are originally present in equal frequency (50%), in which case $BV_i = \frac{1}{2}(Est_i - Est_j)$.

These statistical approaches enable haplotype effect estimates to inform breeding decisions in multiple contexts. Other statistical approaches to calculate breeding values are known to those skilled in the art and can be used in substitution without departing from the spirit and scope of this invention.

In cases where conserved genetic segments, or haplotype windows, are coincident with segments in which QTL have been identified it is possible to deduce with high probability that QTL inferences can be extrapolated to other germplasm having an identical haplotype in that haplotype window. This a priori information provides the basis to select for favorable QTLs prior to QTL mapping within a given population.

For example, plant breeding decisions could comprise:
a) Selection among haploid breeding populations to determine which populations have the highest frequency of favorable haplotypes, wherein haplotypes are designated as favorable based on coincidence with previous QTL mapping and preferred populations undergo doubling; or
b) Selection of haploid progeny containing the favorable haplotypes in breeding populations prior to, or in substitution for, QTL mapping within that population, wherein selection could be done at any stage of breeding and at any generation of a selection and can be followed by doubling; or c) Prediction of progeny performance for specific breeding crosses; or d) Selection of haploid plants for doubling for subsequent use in germplasm improvement activities based on the favorable haplotypes, including line development, hybrid development, selection among transgenic events based on the breeding value of the haplotype that the transgene was inserted into, making breeding crosses, testing and advancing a plant through self fertilization, using plant or parts thereof for transformation, using plants or parts thereof for candidates for expression constructs, and using plant or parts thereof for mutagenesis.

In cases where haplotype windows are coincident with segments in which genes have been identified it is possible to deduce with high probability that gene inferences can be extrapolated to other germplasm having an identical genotype, or haplotype, in that haplotype window. This a priori information provides the basis to select for favorable genes or gene alleles on the basis of haplotype identification within a given population. For example, plant breeding decisions could comprise:

a) Selection among haploid breeding populations to determine which populations have the highest frequency of favorable haplotypes, wherein haplotypes are designated as favorable based on coincidence with previous gene mapping and preferred populations undergo doubling; or b) Selection of haploid progeny containing the favorable haplotypes in breeding populations, wherein selection is effectively enabled at the gene level, wherein selection could be done at any stage of breeding and at any generation of a selection and can be followed by doubling; or c) Prediction of progeny performance for specific breeding crosses; or d) Selection of haploid plants for doubling for subsequent use in germplasm improvement activities based on the favorable haplotypes, including line development, hybrid development, selection among transgenic events based on the breeding value of the haplotype that the transgene was inserted into, making breeding crosses, testing and advancing a plant through self fertilization, using plant or parts thereof for transformation, using plants or parts thereof for candidates for expression constructs, and using plant or parts thereof for mutagenesis.

A preferred haplotype provides a preferred property to a parent plant and to the progeny of the parent when selected by a marker means or phenotypic means. The method of the present invention provides for selection of preferred haplotypes, or haplotypes of interest, and the accumulation of these haplotypes in a breeding population.

In the present invention, haplotypes and associations of haplotypes to one or more phenotypic traits provide the basis for making breeding decisions and germplasm improvement activities. Non-limiting examples of breeding decisions include progeny selection, parent selection, and recurrent selection for at least one haplotype. In another aspect, breeding decisions relating to development of plants for commercial release comprise advancing plants for testing, advancing plants for purity, purification of sublines during development, inbred development, variety development, and hybrid development. In yet other aspects, breeding decisions and germplasm improvement activities comprise transgenic event selection, making breeding crosses, testing and advancing a plant through self-fertilization, using plants or parts thereof for transformation, using plants or parts thereof for candidates for expression constructs, and using plants or parts thereof for mutagenesis.

In another embodiment, this invention enables indirect selection through selection decisions for at least one phenotype based on at least one numerical value that is correlated, either positively or negatively, with one or more other phenotypic traits. For example, a selection decision for any given haplotype effectively results in selection for multiple phenotypic traits that are associated with the haplotype.

In still another embodiment, the present invention acknowledges that preferred haplotypes identified by the methods presented herein may be advanced as candidate genes for inclusion in expression constructs, i.e., transgenes. Nucleic acids underlying haplotypes of interest may be expressed in plant cells by operably linking them to a promoter functional in plants. In another aspect, nucleic acids underlying haplotypes of interest may have their expression modified by double-stranded RNA-mediated gene suppression, also known as RNA interference ("RNAi"), which includes suppression mediated by small interfering RNAs ("siRNA"), trans-acting small interfering RNAs ("ta-siRNA"), or microRNAs ("miRNA"). Examples of RNAi methodology suitable for use in plants are described in detail in U.S. Patent Application Publications 2006/0200878 and 2007/0011775.

Methods are known in the art for assembling and introducing constructs into a cell in such a manner that the nucleic acid molecule for a trait is transcribed into a functional mRNA molecule that is translated and expressed as a protein product. For the practice of the present invention, conventional compositions and methods for preparing and using constructs and host cells are well known to one skilled in the art, see for example, Molecular Cloning: A Laboratory Manual, 3rd edition Volumes 1, 2, and 3 (2000) J. F. Sambrook, D. W. Russell; and N. Irwin, Cold Spring Harbor Laboratory Press. Methods for making transformation constructs particularly suited to plant transformation include, without limitation, those described in U.S. Pat. Nos. 4,971,908, 4,940,835, 4,769,061 and 4,757,011, all of which are herein incorporated by reference in their entirety. Transformation methods for the introduction of expression units into plants are known in the art and include electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; protoplast transformation as illustrated in U.S. Pat. No. 5,508,184; and *Agrobacterium*-mediated transformation as illustrated in U.S. Pat. Nos. 5,635,055; 5,824,877; 5,591,616; 5,981,840; and 6,384,301.

Another preferred embodiment of the present invention is to build additional value by selecting a composition of haplotypes wherein each haplotype has a haplotype effect estimate that is not negative with respect to yield, or is not positive with respect to maturity, or is null with respect to maturity, or amongst the best 50 percent with respect to a phenotypic trait, transgene, and/or a multiple trait index when compared to any other haplotype at the same chromosome segment in a set of germplasm, or amongst the best 50 percent with respect to a phenotypic trait, transgene, and/or a multiple trait index when compared to any other haplotype across the entire genome in a set of germplasm, or the haplotype being present with a frequency of 75 percent or more in a breeding population or a set of germplasm provides evidence of its high value, or any combination of these.

This invention anticipates a stacking of haplotypes from multiple windows into plants or lines by crossing parent plants or lines containing different haplotype regions. The value of the plant or line comprising in its genome stacked haplotype regions is estimated by a composite breeding value, which depends on a combination of the value of the traits and the value of the haplotype(s) to which the traits are linked. The present invention further anticipates that the composite breeding value of a plant or line is improved by modifying the components of one or each of the haplotypes. Additionally, the present invention anticipates that additional value can be built into the composite breeding value of a plant or line by selection of at least one recipient haplotype with a preferred haplotype effect estimate or, in conjunction with the haplotype frequency, breeding value to which one or any of the other haplotypes are linked, or by selection of plants or lines for stacking haplotypes by breeding.

Another embodiment of this invention is a method for enhancing breeding populations by accumulation of one or more preferred haplotypes in a set of germplasm. Genomic regions defined as haplotype windows include genetic information that contribute to one or more phenotypic traits of the plant. Variations in the genetic information at one or more loci can result in variation of one or more phenotypic traits, wherein the value of the phenotype can be measured. The genetic mapping of the haplotype windows allows for a determination of linkage across haplotypes. A haplotype of interest has a DNA sequence that is novel in the genome of the progeny plant and can in itself serve as a genetic marker for the haplotype of interest. Notably, this marker can also be used as an identifier for a gene or QTL. For example, in the event of multiple traits or trait effects associated with the haplotype, only one marker would be necessary for selection purposes. Additionally, the haplotype of interest may provide a means to select for plants that have the linked haplotype region. Selection can be performed by screening for tolerance to an applied phytotoxic chemical, such as an herbicide or antibiotic, or to pathogen resistance. Selection may be performed using phenotypic selection means, such as, a morphological phenotype that is easy to observe such as seed color, seed germination characteristic, seedling growth characteristic, leaf appearance, plant architecture, plant height, and flower and fruit morphology.

The present invention also provides for the screening of progeny haploid plants for haplotypes of interest and using haplotype effect estimates as the basis for selection for use in a breeding program to enhance the accumulation of preferred haplotypes. The method includes: a) providing a breeding population comprising at least two haploid plants wherein the genome of the breeding population comprises a plurality of haplotype windows and each of the plurality of haplotype windows comprises at least one haplotype; and b) associating a haplotype effect estimate for one or more traits for two or more haplotypes from one or more of the plurality of haplotype windows, wherein the haplotype effect estimate can then be used to calculate a breeding value that is a function of the estimated effect for any given phenotypic trait and the frequency of each of the at least two haplotypes; and c) ranking one or more of the haplotypes on the basis of a value, wherein the value is a haplotype effect estimate, a haplotype frequency, or a breeding value and wherein the value is the basis for determining whether a haplotype is a preferred haplotype, or haplotype of interest; and d) utilizing the ranking as the basis for decision-making in a breeding program; and e) at least one progeny haploid plant is selected for doubling on the basis of the presence of the respective markers associated with the haplotypes of interest, wherein the progeny haploid plant comprises in its genome at least a portion of the haplotype or haplotypes of interest of the first plant and at least one preferred haplotype of the second plant; and f) using resulting doubled haploid plants in activities related to germplasm improvement wherein the activities are selected from the group consisting of line and variety development, hybrid development, transgenic event selection, making breeding crosses, testing and advancing a plant through self fertilization, using plant or parts thereof for transformation, using plants or parts thereof for candidates for expression constructs, and using plant or parts thereof for mutagenesis.

Using this method, the present invention contemplates that haplotypes of interest are selected from a large population of plants, and the selected haplotypes can have a synergistic breeding value in the germplasm of a crop plant. Additionally, this invention provides for using the selected haplotypes in the described breeding methods to accumulate other beneficial and preferred haplotype regions and to be maintained in a breeding population to enhance the overall germplasm of the crop plant.

The marker assisted breeding methods and/or methods of associating markers with traits provided herein can be used with one or more individuals, including SSD, from any generation of plant population. Non-limiting examples of plant populations include to F1, F2, BC1, BC2F1, F3:F4, F2:F3, and so on, including subsequent filial generations, as well as experimental populations such as RILs and NILs. It is further anticipated that the degree of segregation within the one or more plant populations of the present invention can vary depending on the nature of the trait and germplasm under evaluation.

Plant Breeding

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). A cultivar is a race or variety of a plant species that has been created or selected intentionally and maintained through cultivation.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

Genotyping can be further economized by high throughput, non-destructive seed sampling. In one embodiment, plants can be screened for one or more markers, such as genetic markers, using high throughput, non-destructive seed sampling. In a preferred aspect, haploid seed is sampled in this manner and only seed with at least one marker genotype of interest is advanced for doubling. Apparatus and methods for the high-throughput, non-destructive sampling of seeds have been described which would overcome the obstacles of statistical samples by allowing for individual seed analysis. For example, U.S. patent application Ser. No. 11/213,430 (filed Aug. 26, 2005); U.S. patent application Ser. No. 11/213,431 (filed Aug. 26, 2005); U.S. patent application Ser. No. 11/213,432 (filed Aug. 26, 2005); U.S. patent application Ser. No. 11/213,434 (filed Aug. 26, 2005); and U.S. patent application Ser. No. 11/213,435 (filed Aug. 26, 2005), U.S. patent application Ser. No. 11/680,611 (filed Mar. 2, 2007), which are incorporated herein by reference in their entirety, disclose apparatus and systems for the automated sampling of seeds as well as methods of sampling, testing and bulking seeds.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

The development of new elite corn hybrids requires the development and selection of elite inbred lines, the crossing of these lines and selection of superior hybrid crosses. The hybrid seed can be produced by manual crosses between selected male-fertile parents or by using male sterility systems. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of Crop Improvement," Longman, Inc., NY, 369-399, 1979; Sneep and Hendriksen, "Plant Breeding Perspectives," Wageningen (ed), Center for Agricultural Publishing and Documentation, 1979; Fehr, In: *Soybeans: Improvement, Production and Uses*, 2nd Edition, Manograph., 16:249, 1987; Fehr, "Principles of Variety Development," *Theory and Technique*, (Vol. 1) and *Crop Species Soybean* (Vol. 2), Iowa State Univ., Macmillan Pub. Co., NY, 360-376, 1987).

An alternative to traditional QTL mapping involves achieving higher resolution by mapping haplotypes, versus individual markers (Fan et al., 2006 Genetics 172:663-686). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well with in the skill of the ordinary practitioner of the art.

It is further understood, that the present invention provides bacterial, viral, microbial, insect, mammalian and plant cells comprising the nucleic acid molecules of the present invention.

As used herein, a "nucleic acid molecule," be it a naturally occurring molecule or otherwise may be "substantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al., 1987 Science 238:336-340; Albarella et al., European Patent 144914), chemical labels (Sheldon et al., U.S. Pat. No. 4,582,789; Albarella et al., U.S. Pat. No. 4,563,417), modified bases (Miyoshi et al., European Patent 119448).

The plant breeding methods provided herein can be used with one or more individuals, including SSD, from any generation of plant population. Non-limiting examples of plant populations include to F1, F2, BC1, BC2F1, F3:F4, F2:F3, and so on, including subsequent filial generations, as well as experimental populations such as RILs and NILs. It is further anticipated that the degree of segregation within the one or more plant populations of the present invention can vary depending on the nature of the trait and germplasm under evaluation.

Having now generally described the invention, the same will be more readily understood through reference to the following examples which are provided by way of illustration, and are not intended to be limiting of the present invention, unless specified.

EXAMPLES

Example 1

Phenotyping for Goss' Wilt

In order to detect QTL associated with resistance to Goss' Wilt, plants were phenotyped to determine Goss' Wilt reaction. The following rating scale was used in order to assess resistance or susceptibility to Goss' Wilt. Phenotypic evaluations of Goss' Wilt reaction is based on percentage of infected leaf area and rated according to a 1 (very resistant) to 9 (susceptible) scale as provided in Table 1. Plants are artificially inoculated and visually rated approximately 3 to 4 weeks after pollination.

TABLE 1

Disease rating scale for Goss' Wilt.

| Description | Rating | Symptoms |
| --- | --- | --- |
| Very Resistant | 1 | 0% of leaf area infected; no visible lesions |
| Very Resistant | 2 | ILA < 1%; few lesions, dispersed through lower leaves |
| Resistant | 3 | 1% ≤ ILA ≤ 20% |
| Resistant | 4 | 20% ≤ ILA ≤ 40% |
| Mid-resistant | 5 | 40% ≤ ILA ≤ 50% |
| Mid-Susceptible | 6 | 50% ≤ ILA ≤ 60%; lesions |
| Susceptible | 7 | 60% ≤ ILA ≤ 75% |
| Susceptible | 8 | 75% ≤ ILA ≤ 90% |
| Susceptible | 9 | >90% of foliar area infected |

ILA = Infected Leaf Area

Example 2

Goss' Wilt Resistance Mapping Study 1

To examine associations between SNP markers and Goss' Wilt resistance, analyzed data from a number of studies was combined. An association study was conducted to evaluate whether significant associations between one or marker genotypes and Goss' Wilt resistance are present in one or more populations. In this association study, data from 10 mapping populations were combined. The number of individuals in the populations ranged from 186 to 369. The number of SNP markers used for screening ranged from 104 to 134. The populations were either F3 or BC1F2. A total of 172 significant associations between SNP markers and Goss' Wilt resistance were identified on Chromosomes 1, 2, 3, 4, 5, 6, 7, 8, 9, and 10. The SNP markers provided can be used to monitor the introgression of Goss' Wilt resistance into a breeding population. Significant marker-Goss' Wilt associations are reported in FIG. 1.

Example 3

Goss' Wilt Resistance Mapping Study 2

An association study was conducted to evaluate whether significant associations between one or marker genotypes and Goss' Wilt resistance are present in one or more populations. In this association study, 988 inbred lines were screened with 1051 SNP markers. A total of 53 significant associations between SNP markers and Goss' Wilt resistance were identified on Chromosomes 1, 2, 3, 4, 5, 6, 8, 9, and 10. The SNP markers provided can be used to monitor the introgression of Goss' Wilt resistance into a breeding population. SNP markers associated with Goss' Wilt resistance, level of significance, and favorable alleles are reported in FIG. 1.

Example 4

Goss' Wilt Resistance Mapping Study 3

An association study was conducted to evaluate whether significant associations between one or more marker genotypes and Goss' Wilt resistance are present in one or more populations. In this study, a rating scale of 1 to 4 was used with 1 being resistant, 2 moderately resistant, 3 moderately susceptible, and 4 susceptible. In this association study, two F3 populations of 154 and 212 individuals were screened with 104 SNP markers. A total of 35 significant associations between SNP markers and Goss' Wilt resistance were identified on Chromosomes 1, 2, 3, 4, 5, 6, 7, 8, 9, and 10. The SNP markers provided can be used to monitor the introgression of Goss' Wilt resistance into a breeding population. SNP markers associated with Goss' Wilt resistance, level of significance, and favorable alleles are reported in FIG. 1.

Example 5

Goss' Wilt Resistance Mapping Study 4

An association study was conducted to evaluate whether significant associations between one or more marker genotypes and Goss' Wilt resistance are present in one or more populations. A population was screened with 518 SNP markers. A total of 80 significant associations between SNP markers and Goss' Wilt resistance were identified on Chromosomes 1, 2, 3, 4, 5, 6, 7, 8, 9, and 10. The SNP markers provided can be used to monitor the introgression of Goss' Wilt resistance into a breeding population. SNP markers associated with Goss' Wilt resistance, level of significance, and favorable alleles are reported in FIG. 1.

Example 6

Exemplary Marker Assays for Detecting Goss' Wilt Resistance

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with Goss' Wilt resistance are given in Table 2.

TABLE 2

Exemplary assays for detecting Goss' Wilt resistance loci.

| Marker | Marker SEQ ID | SNP Position | SEQ ID Forward Primer | SEQ ID Reverse Primer | SEQ ID Probe 1 | SEQ ID Probe 2 |
|---|---|---|---|---|---|---|
| NC0027347 | 896 | 128 | 1332 | 1333 | 1334 | 1335 |
| NC0071001 | 951 | 359 | 1336 | 1337 | 1338 | 1339 |
| NC0017678 | 733 | 171 | 1340 | 1341 | 1342 | 1343 |
| NC0028095 | 1098 | 116 | 1344 | 1345 | 1346 | 1347 |

Example 7

Oligonucleotide hybridization probes useful for detecting corn plants with Goss' Wilt resistance loci Oligonucleotides can also be used to detect or type the polymorphisms associated with Goss' Wilt resistance disclosed herein by hybridization-based SNP detection methods. Oligonucleotides capable of hybridizing to isolated nucleic acid sequences which include the polymorphism are provided. It is within the skill of the art to design assays with experimentally determined stringency to discriminate between the allelic state of the polymorphisms presented herein. Exemplary assays include Southern blots, Northern blots, microarrays, in situ hybridization, and other methods of polymorphism detection based on hybridization. Exemplary oligonucleotides for use in hybridization-based SNP detection are provided in Table 3. These oligonucleotides can be detectably labeled with radioactive labels, fluorophores, or other chemiluminescent means to facilitate detection of hybridization to samples of genomic or amplified nucleic acids derived from one or more corn plants using methods known in the art.

TABLE 3

Exemplary Oligonucleotide Hybridization Probes*.

| Marker | Marker SEQ ID | SNP Position | Probe | SEQ ID Probe |
|---|---|---|---|---|
| NC0027347 | 896 | 128 | GCTACTAGGAAAATGG | 1348 |
| NC0027347 | 896 | 128 | GCTACTAGAAAAATGG | 1349 |
| NC0071001 | 951 | 359 | CAACTACCTAGCATTT | 1350 |
| NC0071001 | 951 | 359 | CAACTACCAAGCATTT | 1351 |
| NC0017678 | 733 | 171 | AGTCAAAGATACTGCA | 1352 |
| NC0017678 | 733 | 171 | AGTCAAAGCTACTGCA | 1353 |
| NC0028095 | 1098 | 116 | TGCCCACATTTGTTAT | 1354 |
| NC0028095 | 1098 | 116 | TGCCCACACTTGTTAT | 1355 |

*SNP nucleotides in bold and underlined.

Example 8

Oligonucleotide Probes Useful for Detecting Corn Plants with Goss' Wilt Resistance Loci by Single Base Extension Methods Oligonucleotides can also be used to detect or type the polymorphisms associated with Goss' Wilt resistance disclosed herein by single base extension (SBE)-based SNP detection methods. Exemplary oligonucleotides for use in SBE-based SNP detection are provided in Table 4. SBE methods are based on extension of a nucleotide primer that is hybridized to sequences immediately adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type certain polymorphisms disclosed in this invention are provided in Table 3 in the columns labeled "Forward Primer SEQ ID" and "Reverse Primer SEQ ID". Following amplification of the region containing the polymorphism, the PCR product is hybridized with an extension primer which anneals to the amplified DNA immediately adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

TABLE 4

Probes (extension primers) for Single Base Extension (SBE) assays.

| Marker | Marker SEQ ID | SNP Position | Probe | SEQ ID Probe |
|---|---|---|---|---|
| NC0027347 | 896 | 128 | TTTTGTACTGCTACTAG | 1356 |
| NC0071001 | 951 | 359 | TACGGAATGCAACTACC | 1357 |
| NC0017678 | 733 | 171 | GTCATGGCGAGTCAAAG | 1358 |
| NC0028095 | 1098 | 116 | TGGATGCTTTGCCCACA | 1359 |

Example 9

Haploid Mapping Study for Goss' Wilt with I208993/LH287 Population

The utility of haploid plants in genetic mapping of traits of interest is further demonstrated in the following example. A mapping population was developed for using haploid plants to map QTL associated with resistance to Goss' Wilt. The population was from the cross of inbred corn lines I208993 by LH287. F1 plants were induced to produce haploid seed. From the I208993/LH287 population, 1384 haploid plants were inoculated with the Goss' Wilt pathogen and phenotyped using a truncated rating scale of 1, 5, or 9. Ratings are done approximately 3 to 4 weeks after pollination. Plants rated either 1 or 9 were used in the QTL mapping. By using only the extreme values (1 or 9), environmental variation that is inherent with disease phenotyping was reduced and a bulk segregate analysis was created from which to detect major QTL. Genotyping was done using 114 SNP markers. Composite interval mapping was conducted to examine significant associations between Goss' Wilt and SNP markers. Table 5 provides markers useful for detecting QTL associated with resistance to Goss' Wilt in the I208993/LH287 haploid mapping population. The chromosome (Chr.) location, chromosome position (Chr. pos), and favorable (Fay.) allele are also provided in Table 5.

It is appreciated by one skilled in the art that the methods of the present invention can be used with one or more individuals, including SSD, from any generation of plant population. Non-limiting examples of plant populations include to F1, F2, BC1, BC2F1, F3:F4, F2:F3, and so on, including subsequent filial generations, as well as experimental populations such as RILs and NILs. It is further anticipated that the degree of segregation within the one or more plant populations of the present invention can vary depending on the nature of the trait and germplasm under evaluation.

population was from the cross of LH295 by I208993. F1 plants were induced to produce haploid seed.

From the I208993/LH295 haploid mapping population, 980 individuals were naturally exposed to the Goss' Wilt pathogen and phenotyped using a modified rating scale of 1, 5, or 9. Plants were rated approximately 3 to 4 weeks after pollination. Plants rated either 1 or 9 were used in the QTL mapping. By using only the extreme values (1 or 9), environmental variation that is inherent with disease phenotyping was reduced and a bulk segregate analysis was created from which to detect major QTL. Genotyping was done with 980 SNP markers. Table 6 provides markers useful for detecting QTL associated with Goss' Wilt in the I208993/LH295 haploid mapping population.

TABLE 5

Markers useful for detecting QTL associated with Goss' Wilt resistance in the I208993/LH287 haploid mapping population.

| Marker | Chr | Chr pos. | Goss' Wilt QTL | Likelyhood ratio | LOD | Additive effect | Fav. allele | SEQ ID | SNP Position* |
|---|---|---|---|---|---|---|---|---|---|
| NC0202383 | 2 | 19 | 22 | 100.304 | 21.78074 | 0.737618 | T | 1229 | 34 |
| NC0199732 | 2 | 37 | 24 | 113.9429 | 24.74239 | 0.779994 | T | 1276 | 138 |
| NC0048553 | 2 | 46.8 | 25 | 103.8964 | 22.56081 | 0.758496 | A | 234 | 485 |
| NC0201646 | 2 | 55.4 | 129 | 96.43437 | 20.94046 | 0.746649 | T | 1294 | 416 |
| NC0201821 | 2 | 71.4 | 27 | 40.13758 | 8.715765 | 0.202738 | T | 1295 | 331 |
| NC0019110 | 2 | 75.1 | 27 | 28.41102 | 6.169374 | 0.173568 | C | 1278 | 153 |
| NC0004821 | 3 | 54.4 | 40 | 47.57959 | 10.33178 | 0.451741 | C | 371 | 294 |
| NC0200643 | 3 | 70.3 | 122 | 47.48045 | 10.31025 | 0.424893 | C | 1296 | 106 |
| NC0040461 | 4 | 51.2 | 125 | 80.02493 | 17.37719 | 0.620383 | A | 1282 | 366 |
| NC0034462 | 4 | 67.8 | 52 | 76.55974 | 16.62474 | 0.574876 | T | 1250 | 301 |
| NC0200535 | 4 | 132 | 58 | 29.47242 | 6.399855 | 0.142544 | T | 1297 | 411 |
| NC0029435 | 4 | 138 | 58 | 29.25183 | 6.351953 | 0.139488 | G | 1298 | 551 |
| NC0011194 | 5 | 29.3 | 63 | 27.51088 | 5.973912 | −0.227689 | C | 1299 | 218 |
| NC0016527 | 5 | 49 | 66 | 29.15712 | 6.331388 | −0.219392 | T | 1255 | 351 |
| NC0202055 | 5 | 76.4 | 68 | 26.18668 | 5.686366 | −0.252002 | T | 1300 | 505 |
| NC0147719 | 5 | 160 | 130 | 47.9265 | 10.40711 | 0.492815 | G | 1301 | 48 |
| NC0012417 | 5 | 175 | 74 | 48.68852 | 10.57258 | 0.505586 | T | 768 | 137 |
| NC0113381 | 6 | 83.8 | 79 | 28.96126 | 6.288858 | −0.21407 | A | 850 | 303 |
| NC0022200 | 6 | 93.7 | 80 | 31.16025 | 6.766361 | −0.201408 | G | 1302 | 153 |
| NC0010347 | 8 | 69.2 | 131 | 27.38218 | 5.945966 | −0.144382 | T | 1015 | 160 |
| NC0199582 | 8 | 86.3 | 99 | 26.24576 | 5.699195 | −0.169537 | A | 1303 | 201 |

*SNP position: refers to the position of the SNP polymorphism in the indicated SEQ ID NO.

Example 10

Haploid Mapping Study for Goss' Wilt with I208993/LH295 Population

The utility of haploid plants in genetic mapping of traits of interest is further demonstrated in the following example. A mapping population was developed for using haploid plants to map QTL associated with resistance to Goss' Wilt. The It is appreciated by one skilled in the art that the methods of the present invention can be used with one or more individuals, including SSD, from any generation of plant population. Non-limiting examples of plant populations include F1, F2, BC1, BC2F1, F3:F4, F2:F3, and so on, including subsequent filial generations, as well as experimental populations such as RILs and NILs. It is further anticipated that the degree of segregation, as well as heterozygosity, within the one or more plant populations of the present invention can vary depending on the nature of the trait and germplasm under evaluation.

TABLE 6

Markers useful for detecting QTL associated with Goss' Wilt in the I208993/LH295 haploid mapping population

| Marker | Chr. | Chr. pos | Goss' Wilt QTL | Likelihood | LOD | Additive Effect | Favorable Allele | SEQ ID | SNP Position* |
|---|---|---|---|---|---|---|---|---|---|
| NC0199051 | 1 | 19.3 | 1 | 28.02118 | 6.084721 | −0.22604 | G | 1274 | 141 |
| NC0105051 | 1 | 31.4 | 3 | 28.79147 | 6.251987 | −0.236914 | C | 24 | 426 |
| NC0032288 | 1 | 133.6 | 10 | 31.20763 | 6.77665 | 0.252864 | C | 1275 | 413 |
| NC0070305 | 1 | 166.5 | 13 | 29.73574 | 6.457033 | 0.216902 | A | 158 | 532 |
| NC0143411 | 2 | 15.4 | 22 | 31.80736 | 6.90688 | −0.372898 | C | 218 | 401 |
| NC0199732 | 2 | 37 | 24 | 51.17309 | 11.11209 | −0.506613 | T | 1276 | 138 |

TABLE 6-continued

Markers useful for detecting QTL associated with Goss' Wilt in the I208993/LH295 haploid mapping population

| Marker | Chr. | Chr. pos | Goss' Wilt QTL | Likelihood | LOD | Additive Effect | Favorable Allele | SEQ ID | SNP Position* |
|---|---|---|---|---|---|---|---|---|---|
| NC0013275 | 2 | 49.7 | 25 | 56.78186 | 12.33002 | −0.677671 | T | 236 | 430 |
| NC0199350 | 2 | 67.8 | 26 | 57.35414 | 12.45429 | −0.577154 | G | 1277 | 226 |
| NC0019110 | 2 | 75.1 | 27 | 51.54673 | 11.19323 | −0.633508 | C | 1278 | 153 |
| NC0027319 | 2 | 93.2 | 29 | 41.90672 | 9.099928 | −0.572435 | T | 272 | 54 |
| NC0104528 | 3 | 24.6 | 37 | 29.36476 | 6.376476 | −0.189689 | G | 1247 | 117 |
| NC0019963 | 3 | 40.6 | 39 | 32.03588 | 6.956503 | −0.139199 | C | 368 | 1173 |
| NC0077220 | 3 | 43.2 | 39 | 27.90631 | 6.059777 | −0.133108 | A | 1279 | 149 |
| NC0108727 | 3 | 77.4 | 122 | 32.5836 | 7.075438 | −0.031362 | C | 375 | 241 |
| NC0039785 | 3 | 94.5 | 123 | 30.35128 | 6.590696 | −0.083537 | T | 401 | 512 |
| NC0031720 | 3 | 99.7 | 123 | 46.9907 | 10.2039 | 0.199348 | G | 408 | 434 |
| NC0200377 | 3 | 116.9 | 43 | 47.01889 | 10.21002 | 0.181809 | A | 1280 | 352 |
| NC0199741 | 3 | 125.7 | 44 | 28.60384 | 6.211245 | −0.315998 | A | 1281 | 294 |
| NC0041040 | 3 | 145.4 | 45 | 36.85657 | 8.003303 | −0.551354 | A | 440 | 497 |
| NC0055502 | 4 | 1.8 | 124 | 36.00788 | 7.819012 | −0.390433 | C | 498 | 105 |
| NC0040461 | 4 | 51.2 | 125 | 42.90587 | 9.316891 | −0.469569 | A | 1282 | 366 |
| NC0199420 | 4 | 102.9 | 55 | 43.93528 | 9.540424 | −0.452635 | G | 1283 | 356 |
| NC0036240 | 4 | 112 | 56 | 38.3635 | 8.330528 | −0.381557 | A | 587 | 441 |
| NC0028933 | 4 | 127.6 | 57 | 29.32225 | 6.367245 | 0.144007 | C | 599 | 355 |
| NC0147712 | 4 | 136.7 | 58 | 33.6318 | 7.303051 | 0.185174 | A | 1284 | 74 |
| NC0028579 | 4 | 155.7 | 60 | 37.46012 | 8.134361 | 0.109588 | A | 629 | 242 |
| NC0029487 | 4 | 171.1 | 126 | 38.35712 | 8.329143 | 0.101598 | G | 1285 | 159 |
| NC0200359 | 5 | 11.7 | 63 | 27.52949 | 5.977952 | −0.167336 | A | 1286 | 196 |
| NC0040571 | 5 | 88.4 | 69 | 59.435 | 12.90615 | −0.58299 | C | 721 | 154 |
| NC0017678 | 5 | 103.8 | 71 | 69.69769 | 15.13466 | −0.722151 | A | 733 | 171 |
| NC0083876 | 5 | 124 | 72 | 29.09207 | 6.317263 | −0.392793 | T | 744 | 513 |
| NC0200343 | 5 | 174.8 | 74 | 27.01332 | 5.865868 | −0.253474 | A | 1287 | 181 |
| NC0027347 | 7 | 43.8 | 86 | 57.87354 | 12.56708 | −0.542521 | A | 896 | 128 |
| NC0201872 | 7 | 64.4 | 88 | 58.07534 | 12.6109 | −0.54188 | C | 1288 | 208 |
| NC0145922 | 7 | 80.5 | 89 | 26.87412 | 5.835642 | −0.271008 | G | 940 | 451 |
| NC0071001 | 7 | 99.4 | 90 | 26.59882 | 5.775861 | −0.262452 | T | 951 | 359 |
| NC0199879 | 7 | 112.1 | 92 | 34.51543 | 7.494931 | −0.28773 | A | 1289 | 228 |
| NC0200055 | 7 | 122.3 | 127 | 36.14355 | 7.848472 | −0.277751 | T | 1290 | 116 |
| NC0110771 | 7 | 138.5 | 93 | 32.98577 | 7.162769 | −0.163457 | A | 976 | 490 |
| NC0200495 | 7 | 155.9 | 95 | 27.69812 | 6.014571 | −0.118782 | G | 1291 | 302 |
| NC0028095 | 9 | 59.4 | 107 | 29.92602 | 6.498353 | 0.142796 | C | 1098 | 116 |
| NC0144850 | 9 | 67 | 108 | 30.50354 | 6.62376 | 0.146897 | G | 1292 | 244 |
| NC0030134 | 10 | 79.4 | 120 | 27.87616 | 6.05323 | −0.317779 | TCCACTAT | 1215 | 94 |
| NC0200312 | 10 | 85.7 | 128 | 31.10615 | 6.754615 | −0.355789 | A | 1293 | 89 |

*SNP position: refers to the position of the SNP polymorphism in the indicated SEQ ID NO.

Example 11

Introgression of Goss' Wilt Resistance Using SNP Markers

Loci associated with resistance to Goss' Wilt can be introgressed into corn plants by methods known to those skilled in the art of plant breeding. A plant breeder can use SNP markers to monitor the introgression of Goss' Wilt resistance loci and to select for lines carrying the favorable allele for one or more of said SNP markers. In this example, the inbred line LH287 is used as a source of Goss' Wilt resistance. SNP markers used to monitor introgression of Goss' Wilt resistance loci on Chromosome 2 include NC0202383, NC0199732, NC0048553, and NC0201646 (SEQ ID NOs: 1122, 1276, 1294, and 234). SNP used to monitor introgression of Goss' Wilt resistance loci on Chromosome 3 include NC0019963 and NC0004821 (SEQ ID NOs: 368 and 371). SNP markers used to monitor the introgression of Goss' Wilt resistance loci on Chromosome 4 include NC0040461 and NC0034462 (SEQ ID NOs: 1282 and 1250). SNP markers used to monitor the introgression of Goss' Wilt resistance loci on Chromosome 5 include NC0147719 and NC0012417 (SEQ ID NOs: 1301 and 768). The favorable allele is the allele associated with the resistant donor parent.

In a further illustration, the inbred line LH295 is used as a source of Goss' Wilt resistance. SNP markers used to monitor the introgression of Goss' Wilt resistance loci on Chromosome 2 include NC0013275, NC0199350, and NC0019110 (SEQ ID NOs: 236, 1277, and 1278). SNP markers used to monitor the introgression of Goss' Wilt resistance loci on Chromosome 3 include NC0199741 and NC0041040 (SEQ ID NOs: 1281 and 440). SNP markers used to monitor the introgression of Goss' Wilt resistance loci on Chromosome 4 include NC0040461, NC0199420, and NC0036240 (SEQ ID NOs: 1282, 1283, and 587). SNP markers used to monitor the introgression of Goss' Wilt resistance loci on Chromosome 5 include NC0040571 and NC0017678 (SEQ ID NOs: 721 and 733). SNP markers used to monitor the introgression of Goss' Wilt resistance loci on Chromosome 7 include NC0201872 and NC0145922 (SEQ ID NOs: 1288 and 940). SNP markers used to monitor the introgression of Goss' Wilt resistance loci on Chromosome 10 include NC0200312 (SEQ ID NO: 1293). A plant breeder can use SNP markers to monitor the introgression of Goss' Wilt resistance loci and to select for lines carrying the favorable allele for one or more of said SNP markers.

The introgression of one or more resistance loci is achieved via repeated backcrossing to a recurrent parent accompanied by selection to retain one or more Goss' Wilt resistance loci from the donor parent using the above-described markers.

This backcross procedure is implemented at any stage in line development and occurs in conjunction with breeding for superior agronomic characteristics or one or more traits of interest, including transgenic and nontransgenic traits.

Alternatively, a forward breeding approach is employed wherein one or more Goss' Wilt resistance loci can be monitored for successful introgression following a cross with a susceptible parent with subsequent generations genotyped for one or more Goss' Wilt resistance loci and for one or more additional traits of interest, including transgenic and nontransgenic traits.

Example 12

Application of Markers Associated with Goss' Wilt in a Corn Breeding Program

From the studies presented in FIG. 1, it is apparent that a chromosomal region can have multiple SNP markers associated with Goss' Wilt resistance. Following are non-limiting examples of targeting at least one marker from at least on locus associated with Goss' Wilt resistance for the purpose of breeding corn resistant to Goss' Wilt. Specifically the markers of the present invention have utility for generating corn inbreds and hybrids resistant to Goss Wilt. The markers of the present invention are useful in parent selection, progeny selection, and marker-assisted introgression and backcrossing. Exemplary markers from Chromosome 1 are NC0004909 and NC0005098 (SEQ ID NOs: 175 and 177). Exemplary markers from Chromosome 3 are NC0146497 and NC0155987 (SEQ ID NOs: 479 and 480). Exemplary markers from Chromosome 4 are NC0077408, NC0003274, and NC0009280 (SEQ ID NOs: 582, 585, and 1251). Exemplary markers from Chromosome 8 are NC0010392, NC0012656, and NC0008831 (SEQ ID NOs: 1053, 1054, and 1056).

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

Various patent and non-patent publications are cited herein, the disclosures of each of which are, to the extent necessary, incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09119365B2). An electronic copy of the "Sequence Listing" will also be available from the USPTO upon request and payment of the fee set forth in 37 CFR 1.19(b)(3).

We claim:

1. A method of creating a population of corn plants comprising at least one allele associated with Goss' Wilt resistance comprising SEQ ID NO: 224, 228, 231, 232, 233, or 234, the method comprising the steps of:
   a) genotyping a first population of corn plants, said population containing at least one allele associated with Goss' Wilt resistance, the at least one allele associated with Goss' Wilt comprising SEQ ID NO: 224, 228, 231, 232, 233, or 234;
   b) selecting from said first population based upon said genotyping one or more identified corn plants containing said at least one allele associated with Goss' Wilt comprising SEQ ID NO: 224, 228, 231, 232, 233, or 234; and
   c) growing from said selected corn plants a second population, thereby creating a population of corn plants comprising at least one allele associated with Goss' Wilt resistance comprising SEQ ID NO: 224, 228, 231, 232, 233, or 234.

2. A method of introgressing a Goss' Wilt resistance QTL allele into a corn plant, the method comprising the steps of:
   a) crossing at least one first corn plant comprising the Goss' Wilt resistance QTL allele, wherein the allele comprises SEQ ID NO: 224, 228, 231, 232, 233, or 234, with at least one second corn plant in order to form a segregating population;
   b) screening said segregating population with one or more nucleic acid markers to determine if one or more corn plants from said segregating population contain the Goss' Wilt resistance QTL allele comprising SEQ ID NO: 224, 228, 231, 232, 233, or 234; and
   c) selecting from said segregating population one or more corn plants comprising said allele associated with Goss' Wilt resistance QTL.

3. The method according to claim 1, wherein the first population of corn plants genotyped in step (a) is a population generated by a cross.

4. The method of claim 3, wherein said cross is effected by mechanical emasculation, chemical sterilization, or genetic sterilization of a pollen acceptor.

5. The method of claim 1, wherein said genotyping is effected in step (a) by determining the allelic state of at least one corn genomic DNA marker.

6. The method according to claim 1, wherein said selected corn plant(s) of step (b) exhibit at least partial resistance to a Goss' Wilt-inducing bacteria or at least substantial resistance to a Goss' Wilt-inducing bacteria.

7. The method of claim 3, wherein said first population of corn plants is generated by a cross of at least one Goss' Wilt resistant corn plant with at least one Goss' Wilt sensitive corn plant.

8. The method of claim 3, wherein said first population of corn plants is a segregating population.

9. The method of claim 3, wherein said cross is a back cross of at least one Goss' Wilt resistant corn plant with at least one Goss' Wilt sensitive corn plant to introgress Goss' Wilt resistance into a corn germplasm.

10. The method of claim 3, wherein said first population is a haploid breeding population.

11. The method according to claim 2, wherein at least one of the one or more nucleic acid markers is located within 5 cM of said Goss' Wilt resistance QTL.

12. The method according to claim 11, wherein at least one of the one or more nucleic acid markers is located within 2 cM of said Goss' Wilt resistance QTL.

13. The method according to claim 12, wherein at least one of the one or more nucleic acid markers is located within 1 cM of said Goss' Wilt resistance QTL.

14. The method according to claim 2, wherein at least one of the one or more nucleic acid markers exhibits a LOD score of greater than 4.0 with said Goss' Wilt resistance QTL.

15. The method according to claim 14, wherein said one or more nucleic acid marker is SEQ ID NO: 224.

* * * * *